(12) United States Patent
Satake et al.

(10) Patent No.: US 10,036,737 B2
(45) Date of Patent: Jul. 31, 2018

(54) ANALYSIS SYSTEM

(71) Applicant: Hitachi High-Technologies Corporation, Minato-ku, Tokyo (JP)

(72) Inventors: Hiroyuki Satake, Tokyo (JP); Yuichiro Hashimoto, Tokyo (JP); Masao Suga, Tokyo (JP); Hideki Hasegawa, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 179 days.

(21) Appl. No.: 14/782,424

(22) PCT Filed: Apr. 10, 2014

(86) PCT No.: PCT/JP2014/060397
§ 371 (c)(1),
(2) Date: Oct. 5, 2015

(87) PCT Pub. No.: WO2014/171390
PCT Pub. Date: Oct. 23, 2014

(65) Prior Publication Data
US 2016/0025692 A1    Jan. 28, 2016

(30) Foreign Application Priority Data
Apr. 15, 2013    (JP) .................................. 2013-084950

(51) Int. Cl.
*G01N 30/72* (2006.01)
*G01N 27/62* (2006.01)
*H01J 49/00* (2006.01)

(52) U.S. Cl.
CPC ....... *G01N 30/7233* (2013.01); *G01N 27/624* (2013.01); *H01J 49/004* (2013.01); *H01J 49/0027* (2013.01)

(58) Field of Classification Search
CPC .............. G01N 27/624; G01N 30/7233; H01J 49/0027; H01J 49/004
See application file for complete search history.

(56) References Cited

U.S. PATENT DOCUMENTS

| 2003/0052263 A1 | 3/2003 | Kaufman et al. |
| 2005/0063864 A1* | 3/2005 | Sano .................. G01N 33/6848 422/68.1 |

(Continued)

FOREIGN PATENT DOCUMENTS

| JP | 2005-513414 A | 5/2005 |
| JP | 2006-53004 A | 2/2006 |

(Continued)

OTHER PUBLICATIONS

Dolan et al., Variability of column selectivity for reversed-phase high-performance liquid chromatography Compensation by adjustment of separation conditions, 2002, Journal of Chromatography A, 960, pp. 51-67.*

(Continued)

*Primary Examiner* — Son Le
*Assistant Examiner* — David Z Huang
(74) *Attorney, Agent, or Firm* — Crowell & Moring LLP

(57) ABSTRACT

An analysis system is provided with: a storage unit that stores first information associating mass spectrometry result information with an analysis condition concerning ion mobility separation; and a control unit that determines, as a first analysis condition for an ion to be measured, the analysis condition associated with the mass spectrometry result information of the first information corresponding to the mass spectrometry result information of the ion to be measured.

13 Claims, 22 Drawing Sheets

(56) References Cited

U.S. PATENT DOCUMENTS

2006/0219896 A1* 10/2006 Hashimoto ......... H01J 49/4225
  250/288
2009/0266983 A1  10/2009 Yamamoto et al.
2010/0237233 A1   9/2010 Covey et al.

FOREIGN PATENT DOCUMENTS

| JP | 2009-2815 A | 1/2009 |
| JP | 2009-264970 A | 11/2009 |
| JP | 2012-521072 A | 9/2012 |
| WO | WO 03/005016 A1 | 1/2003 |

OTHER PUBLICATIONS

International Search Report (PCT/ISA/210) issued in counterpart International Application No. PCT/JP2014/060397, dated Jun. 10, 2014 (Four (4) pages).

Sugai, "Fundamentals of Mass Spectrometry—Ion Mobility Spectrometry-", Journal of the Mass Spectrometry Society of Japan, Apr. 1, 2010, vol. 58, No. 2, pp. 47-73, with English Abstract (Twenty-seven (27) pages).

Guevremont, "High-field asymmetric waveform ion mobility spectrometry: A new tool for mass spectrometry", Journal of Chromatography A, vol. 1058, 2004, pp. 3-19, (Seventeen (17) pages).

\* cited by examiner

Mass spectrometry data obtained by single LC/MS analysis

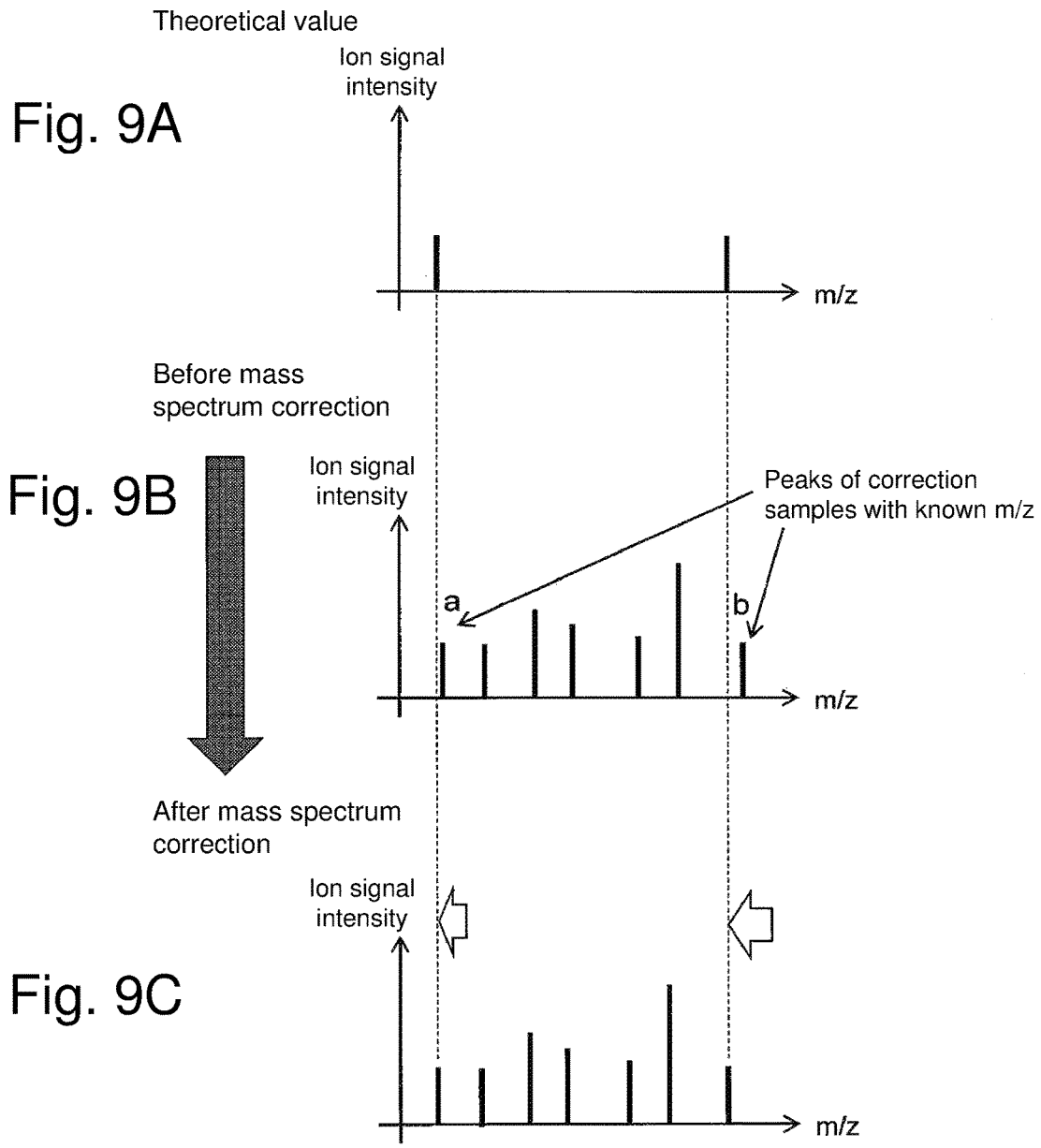

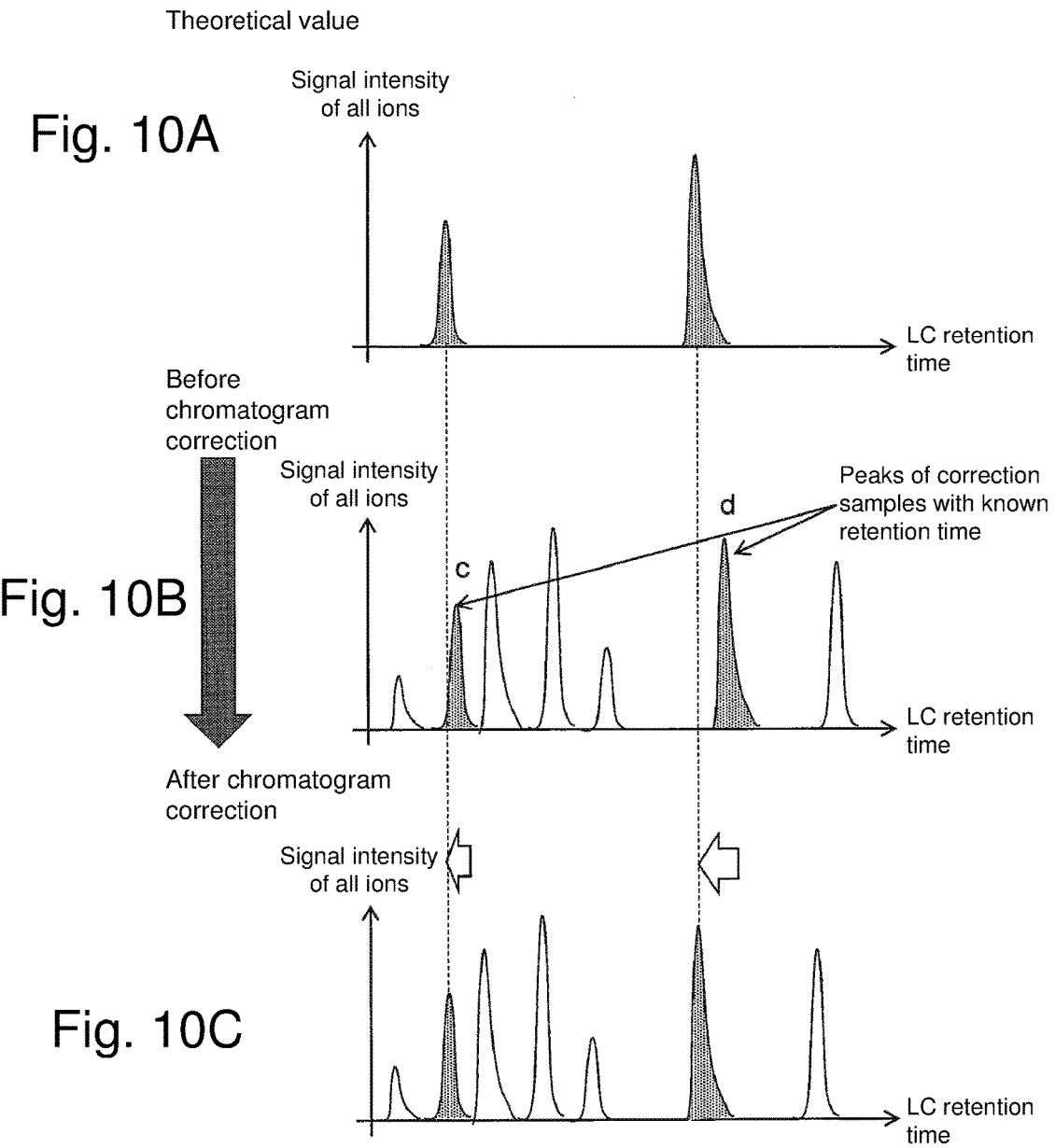

Second or subsequent LC/MS analysis

ANALYSIS SYSTEM

TECHNICAL FIELD

The present invention relates to an ion mobility separation technology and an ion mass analysis technology.

BACKGROUND ART

Mass spectrometry is a method of separating ions based on the mass-to-charge ratio (m/z) of molecular ions in vacuum, capable of separating and detecting ions with high sensitivity and high accuracy. The mass spectrometry technology is generally used for detectors in a liquid chromatograph (hereafter "LC") or gas chromatograph (hereafter "GC"), often involving an analysis technique called liquid chromatography/mass spectrometry (hereafter "LC/MS") or gas chromatography/mass spectrometry (hereafter "GC/MS"). In recent years, progress has been made in the development of tandem mass spectrometry which decomposes an ion as the object of measurement and measures the decomposed ion, and high-resolution mass spectrometers such as a time-of-flight mass spectrometer and a Fourier transform mass spectrometer. These technologies are becoming widely available in biotechnology and medical fields in particular.

Meanwhile, ion mobility spectrometry (hereafter "IMS") is a method for ion separation in a gas phase under atmospheric pressure. Ion mobility spectrometry separates ions by utilizing the difference in the speed of ion movement in a gas phase due to difference in ion structure from one ion to another. Thus, ion mobility spectrometry is capable of separation in principle even between different kinds of ions having the same m/z. Because ion mobility spectrometry is a different separation method from mass spectrometry, a measurement method combining mass spectrometry and ion mobility spectrometry has been reported. An example of ion mobility spectrometry is a field asymmetric waveform ion mobility separation device (field asymmetric waveform ion mobility spectrometry; hereafter "FAIMS").

CITATION LIST

Patent Literature

Patent Literature 1: JP 2005-513414 A

SUMMARY OF INVENTION

Technical Problem

In the ion mobility separation device that separates and detects ions using ion mobility, the art of detecting ions generated by an ion source with high throughput is important. Patent Literature 1 describes a method for identifying the ion species from a detection result in two or more different electric field states in a field asymmetric waveform ion mobility separation device (FAIMS).

According to the technique of Patent Literature 1, with respect to one type of ion to be measured, the two parameters of a separation voltage and a compensation voltage, for example, are set at a plurality of points for measurement. Accordingly, one type of ion is measured under a plurality of conditions, requiring much measurement time. As a result, when ions to be measured move to the FAIMS one after another, as in the case of LC/MS analysis, as long as time is being taken by one ion species, another ion species cannot be measured, resulting in a decrease in measurement throughput. In this technique, by performing measurement finely at fine voltage pitches or widely in a wide range of voltages (i.e., by performing measurement under a wide range of analysis conditions), more precise measurement can be performed. However, this requires a longer measurement time.

The present invention was made in view of the above circumstance, and provides an analysis condition determination technology for performing an analysis process in an ion mobility device with increased efficiency.

Solution to Problem

In order to solve the problem, the configurations set forth in the claims are adopted, for example. While the present application includes a plurality of means for solving the problem, one example provides an analysis system including a storage unit that stores first information associating mass spectrometry result information with an analysis condition concerning ion mobility separation; and a control unit that determines, as a first analysis condition for an ion to be measured, the analysis condition associated with the mass spectrometry result information of the first information corresponding to the mass spectrometry result information of the ion to be measured.

Advantageous Effects of Invention

According to the present invention, in an ion mobility device, an analysis condition suitable for an ion to be measured can be determined in a short time, and an analysis process can be performed with increased efficiency.

Additional features related to the present invention will become apparent from the following description and the attached drawings. Other problems, configurations, or effects will become apparent from the following description of embodiments.

BRIEF DESCRIPTION OF DRAWINGS

FIG. 9 illustrates diagrams for describing an m/z correction method.

FIG. 10 illustrates diagrams for describing an LC retention time correction method.

DESCRIPTION OF EMBODIMENTS

In the following, embodiments of the present invention will be described with reference to the attached drawings. While the attached drawings show specific embodiments in accordance with the principle of the present invention, the embodiments are for facilitating an understanding of the present invention and not to be used for interpreting the present invention in a limited sense.

Figure 1A:
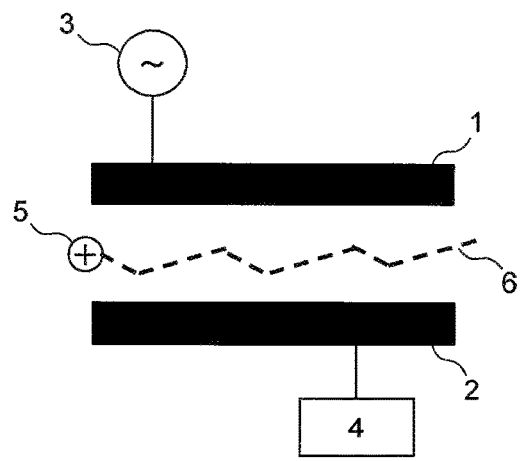
FIG. 1A illustrates a typical configuration of an FAIMS.

FIG. 1A illustrates a typical configuration of a FAIMS. The FAIMS is provided with two flat-plate electrodes of metal, i.e., a first electrode 1 and a second electrode 2. The FAIMS is also provided with an alternating-current voltage power supply 3 and a direct-current voltage power supply 4.

Figure 1B:
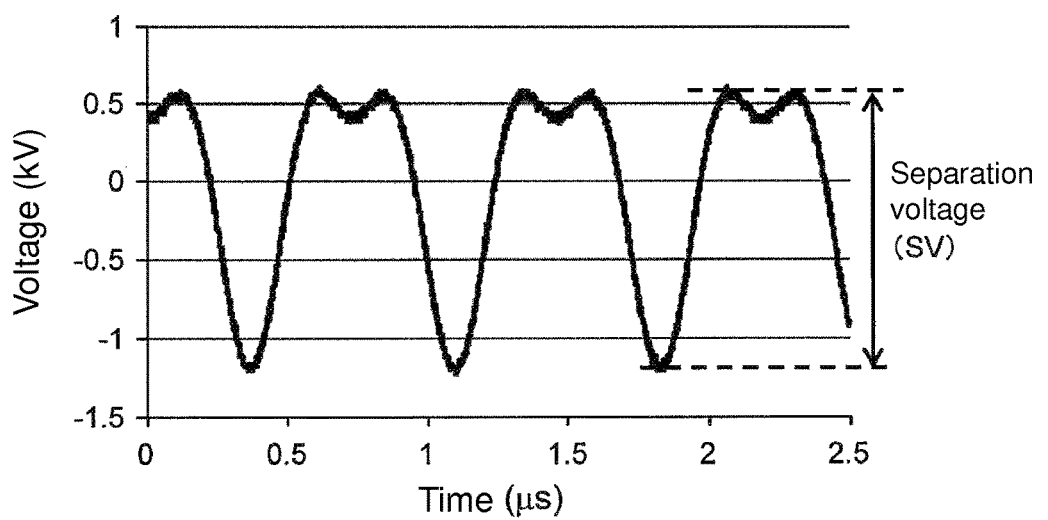
FIG. 1B illustrates a separation voltage waveform in FAIMS.

In the FAIMS, a separation voltage (SV, or dispersion voltage), which is a superposition of high frequency voltages, is applied to the first electrode 1 by the alternating-current voltage power supply 3, whereby a high frequency electric field is applied between the first electrode 1 and the second electrode 2. As illustrated in FIG. 1B, the separation voltage (SV) includes a high voltage (plus voltage) and a low voltage (minus voltage) each repeatedly applied for a certain period such that, when time-averaged, the separation voltage is 0. A compensation voltage (CV, or correction voltage), which is a constant voltage generated by the direct-current voltage power supply 4, is applied to the second electrode 2 so as to correct an ion trajectory 6 of an ion 5 and to enable only a specific ion to pass through.

First Embodiment

A first embodiment will be described. In the present embodiment, a method of determining a separation analysis condition for a field asymmetric waveform ion mobility spectrometry device (hereafter FAIMS) using a database, and an analysis method under the condition will be described.

Figure 2:
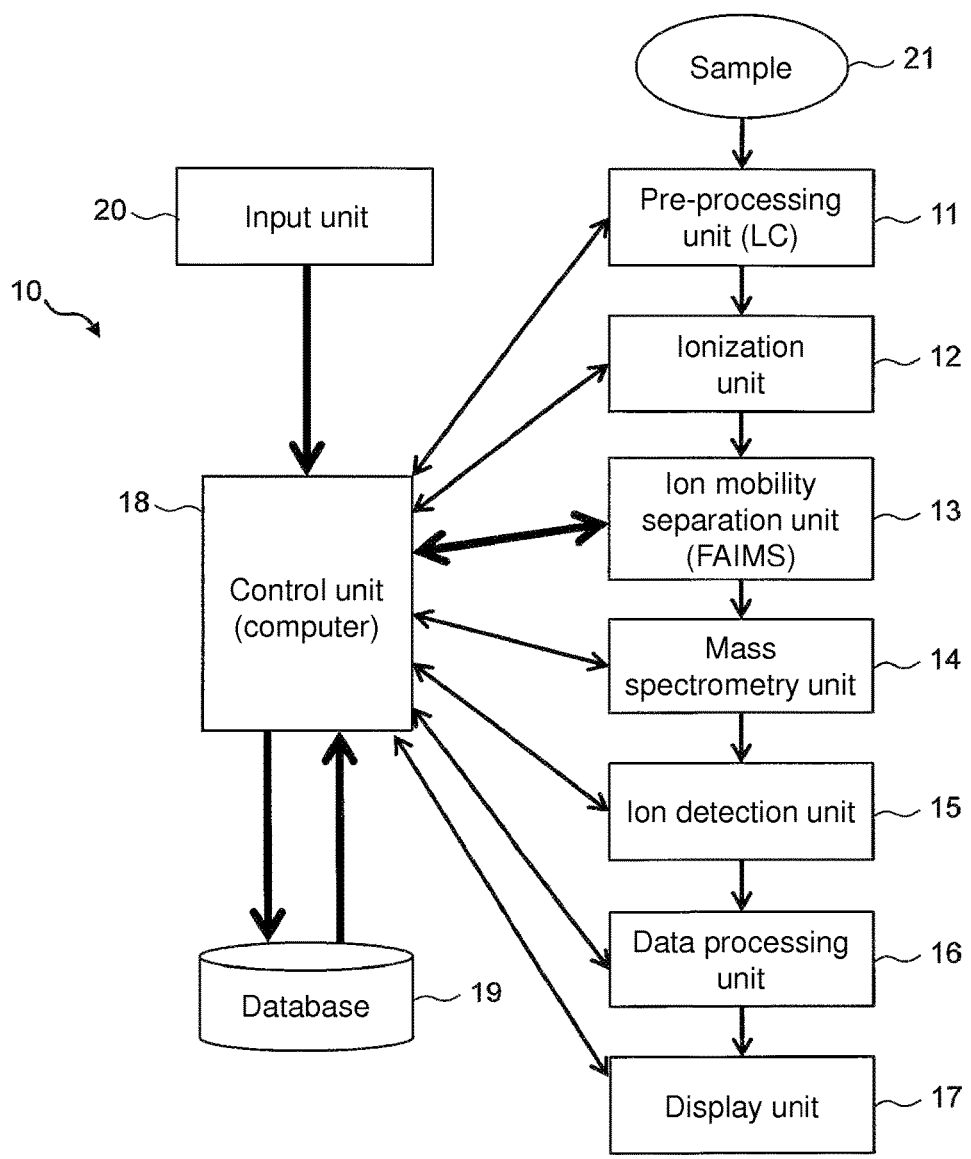
FIG. 2 illustrates a diagram for describing the configuration of a mass spectrometry system.

FIG. 2 illustrates a configuration of a mass spectrometry system using the FAIMS and a mass spectrometer.

The mass spectrometry system 10 is provided with a pre-processing unit 11, an ionization unit 12, an ion mobility separation unit (FAIMS) 13, a mass spectrometry unit 14, an ion detection unit 15, a data processing unit 16, a display unit 17, a control unit 18, a database 19, and an input unit 20. While the ion mobility separation unit 13 will be described as being a field asymmetric waveform ion mobility spectrometry device (FAIMS) by way of example, other forms of ion mobility separation may be used.

The flow of analysis will be described. First, a sample 21 as the object of analysis is pre-processed in the pre-processing unit 11. The pre-processing may include, for example, a combination of deproteinization process, desalination, centrifugal separation, enzyme digestion process, solid phase extraction process, a liquid separation device using an LC (hereafter LC), and gas separation device using a GC.

The pre-processed sample 21 is ionized in the ionization unit 12. Thereafter, the sample ion is separated in the ion mobility separation unit (FAIMS according to the present embodiment) 13 and passed through. The sample ion is then subjected to mass separation in the mass spectrometry unit 14 in accordance with the mass-to-charge ratio (m/z) of the ion, where m is the mass of ion, and z is the charge amount of ion or a charge valence.

The mass-separated ion is detected by the ion detection unit 15 and data-processed in the data processing unit 16. The data processing unit 16 produces a process result in the form of mass spectrometry data, such as a mass spectrometry spectrum, which is displayed on the display unit 17. The input unit 20 may be used to input various parameters, such as analysis conditions (voltages, gas flow rates, time and the like) in the pre-processing unit 11, the ion mobility separation unit 13, and the mass spectrometry unit 14.

The control unit 18 controls the various constituent elements of the mass spectrometry system 10, and may include an information processing device such as a personal computer. The control unit 18 is provided with a central operating and processing device, an auxiliary storage device, a main storage device, and the above-described display unit 17 and input unit 20. For example, the central operating and processing device includes a processor (or an operating unit), such as a Central Processing Unit (CPU). For example, the auxiliary storage device is a hard disk, while the main storage device is a memory. The display unit 17 may include a display and the like, and the input unit 20 may include a keyboard and a pointing device (such as a mouse).

The database 19 is stored in the storage device. In the database 19, a table (first information) associating mass spectrometry result information with an analysis condition concerning ion mobility separation is stored. In the following example, the mass spectrometry result information in the database 19 includes a mass-to-charge ratio (m/z) and an ion charge amount (z). The analysis condition concerning ion mobility separation includes a separation voltage (SV) and a compensation voltage (CV). While in the following, the information will be expressed in table structure in the database, the information may not be necessarily expressed in table data structure. For example, other data structures, such as a list or a queue, or other forms of expression may be used. In order to indicate data structure independency, "table", "list", "queue" and the like may be simply referred to as "information".

In mass spectrometry measurement at a certain time, a mass spectrum with the horizontal axis showing m/z and the vertical axis showing signal intensity is obtained. In the case of LC/MS analysis, there is additionally the axis for LC retention time, so that a mass spectrum is obtained at each LC retention time, as illustrated in FIG. 3.

Figure 3:
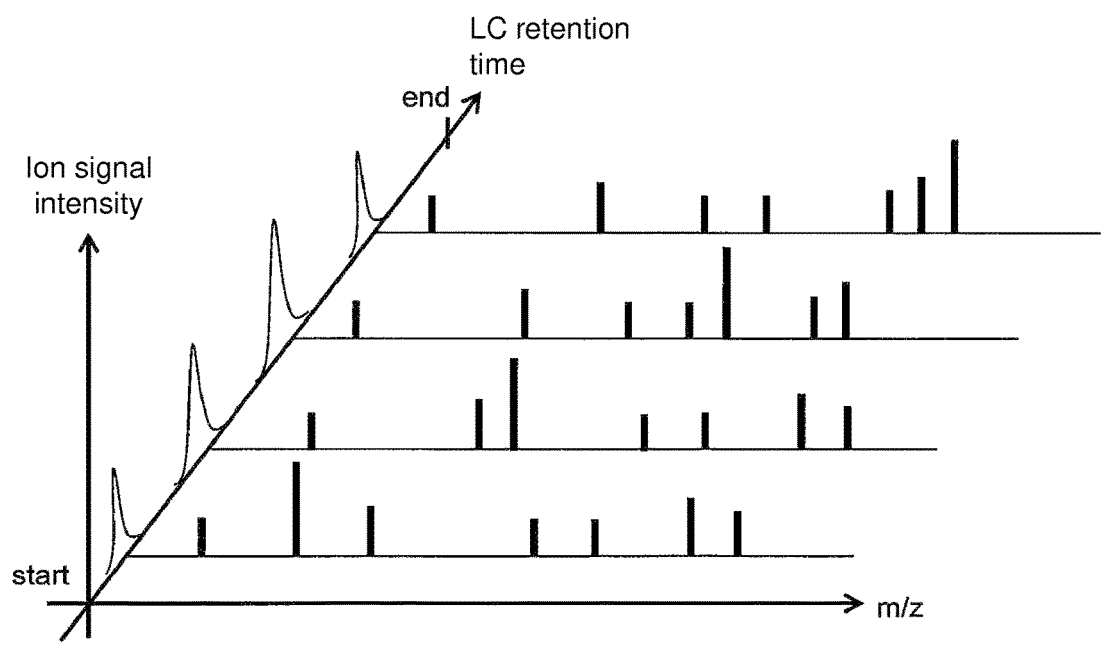
FIG. 3 illustrates mass spectrometry data obtained by an LC/MS analysis.

In FIG. 3, the mass spectrum (the horizontal axis showing m/z and the vertical axis showing signal intensity) is shown only where there is a peak on an ion chromatogram (plane of the LC retention time and the ion signal intensity). However, the mass spectrum is acquired at all times, so that mass spectrum data are acquired even where there is no peak. FIG. 3 concerns a single LC/MS analysis, where the timing at which the sample 21 is injected once and sample delivery by an LC delivery pump is started is the start, and the timing at which the sample delivery by the LC delivery pump ends is the end.

In the LC in the pre-processing unit 11, the sample 21 is passed through a column capable of adsorption, whereby the sample (molecular species) can be separated in time. The sample 21 has a different retention force with respect to the column used in the LC due to different chemical properties, enabling its separation in time. For example, when ions of two types of molecular species but with the same m/z happen to exist, the two molecular species are together subjected to mass spectrometry. Thus, unless the LC is used, it would be impossible to separate and measure the respective molecular species, and it would therefore be difficult to quantitate each molecular species.

By using an LC, even for ions of two molecular species with the same m/z, the ions can be separated in time and individually measured because of their different chemical properties and hence different retention times. The "LC retention time" refers to the time in which the sample is eluted from the LC column, i.e., the time in which the sample passes through the LC column and is subjected to mass spectrometry (see FIG. 3). In the chromatogram of the plane consisting of the two axes for LC retention time and ion signal intensity in FIG. 3, the signal intensity of all ions is plotted. As described above, the retention time differs depending on the chemical property of the sample 21, so that if the retention time is different, the molecular species is different. Accordingly, while there is a plurality of peaks on the chromatogram, each peak corresponds to a separate ion species.

Figure 4:
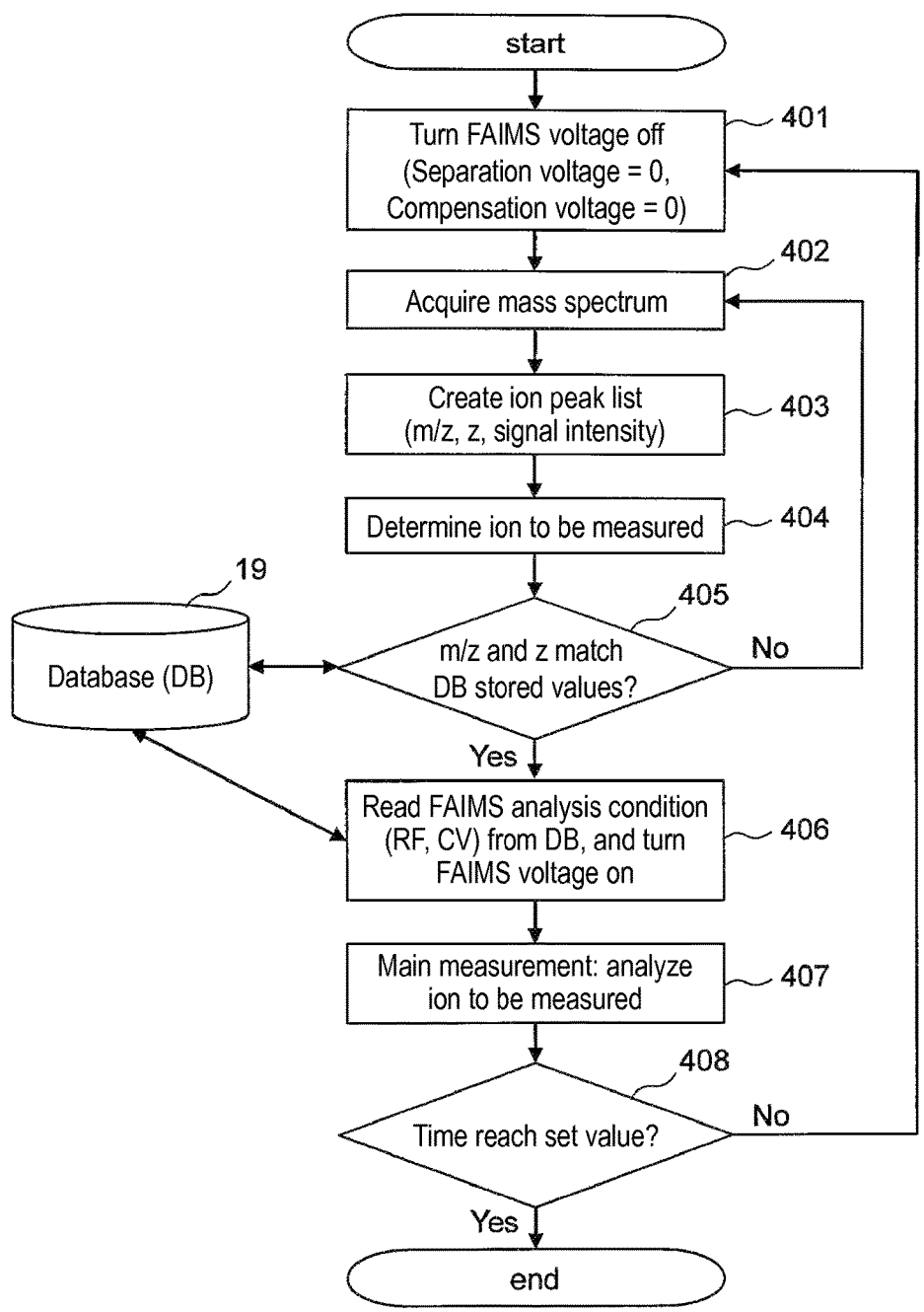
FIG. 4 illustrates an example of a measurement flow in the mass spectrometry system according to a first embodiment.
Figure 5:
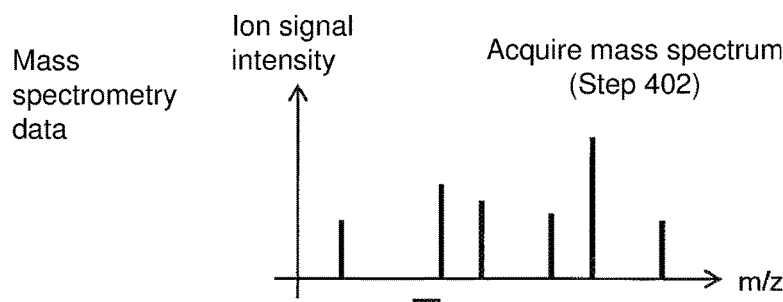
FIG. 5 illustrates diagrams for describing steps 402 to 406 of FIG. 4.

FIG. 4 illustrates an example of the measurement flow of the mass spectrometry system according to the first embodiment. The measurement flow of FIG. 4 is a flow mainly in the portions of the ion mobility separation unit 13, the mass spectrometry unit 14, and the ion detection unit 15. FIG. 5 illustrates diagrams for describing the flow of FIG. 4. In the following, with reference to FIG. 4 and FIG. 5, the flow of analysis according to the present embodiment will be described. The agent of the following process is the control unit 18. The control unit 18 executes the following process while controlling the ion mobility separation unit 13, the mass spectrometry unit 14, and the ion detection unit 15.

As described above, the start of the flowchart corresponds to the timing at which the sample is injected and sample delivery by a delivery pump of the LC is started. The end corresponds to the timing at which the sample delivery by the LC delivery pump ends (see FIG. 3).

In step 401, as an analysis condition for the FAIMS, i.e., the ion mobility separation unit 13, the separation voltage and the compensation voltage are set to 0 V. Thereby, ions of various mass-to-charge ratios (m/z) are allowed to pass through the FAIMS. Thus, in the later-stage mass spectrometry unit 14, a mass spectrum of a wide range of m/z can be acquired.

In step 402, a mass spectrum of a wide range of m/z is acquired so as to search for an ion to be measured for the main measurement. The mass spectrum is obtained at each LC retention time, as described above, so that in the single LC/MS analysis, a number of mass spectra are obtained as illustrated in FIG. 3. FIG. 5(A) illustrates an example of the mass spectrum acquired in step 402.

In step 403, peaks of the mass spectrum data acquired in step 402 are determined, and a peak list is created. By extracting peaks observed in real-time within a very short time (within 100 ms) during analysis and creating the peak list, the analysis can proceed in real-time. In the present example, as illustrated in FIG. 5(B), peaks are extracted from the mass spectrum, and the peak list including mass-to-charge ratio (m/z), charge amount (z), and ion signal intensity (I) is created.

A peak extraction condition may include extracting the ion signal intensity equal to or greater than a predetermined threshold value as a peak. Only a signal intensity equal to or greater than a threshold value set by the user via the input unit 20 may be extracted as a peak. In this way, small signal intensity peaks, such as a noise peak, can be eliminated. In another method, a peak may be extracted when the ratio of ion signal intensity to noise (signal to noise ratio: S/N) is equal to or greater than a certain threshold value. Further, the peak extraction method may include other known methods.

In step 404, the ion to be measured is determined from the created peak list. In one example of the determination method, an ion with the maximum ion signal intensity (I) is selected. That is, in the column for ion signal intensity (I) in the peak list, an ion with the maximum value is determined to be the ion to be measured. In the example of FIG. 5(B), the signal intensity L is the maximum value, so that the ion having the information (J, K, L) in the peak list provides the ion to be measured. After the ion to be measured is determined, the ion signal intensity information (L) is not necessary. Thus, the information may be deleted from the information of the ion to be measured at this point in time. Namely, the information of the ion to be measured becomes (J, K) from (J, K, L).

In step 405, a comparison is made to determine whether the one ion to be measured (J, K) determined in step 404 is registered in the database 19. That is, it is confirmed whether the ion to be measured (J, K) matches values stored in the database 19. In the database 19, sets of mass-to-charge ratio (m/z), charge amount (z), FAIMS separation voltage (SV), and compensation voltage (CV) are stored. Of these four parameters, it is determined whether the set (J, K), i.e., the information of the ion to be measured that has been determined, is stored in the columns for the set (m/z, z).

In the example of FIG. 5C, there is the matching information (J, K) in the information stored in the database 19. Thus, the process proceeds from step 405 to step 406 (Yes in step 405). If the difference between the ion to be measured (J, K) and the stored values in the database 19 is within a predetermined allowable range, a match may be recognized. On the other hand, if there was no matching information in the database 19, the process returns to step 402 (No in step 405), and steps 403, 404, and 405 are again implemented.

In, step 406, the FAIMS analysis condition is read from the database 19. In the example of FIG. 5C, the set of the separation voltage (SV) and the compensation voltage (CV)

associated with (J, K), i.e., (X, Y), is read. Then, the separation voltage (X) and the compensation voltage (Y) are respectively applied to the first electrode 1 and the second electrode 2 of the FAIMS. It is also possible to apply the separation voltage and the compensation voltage to the same electrode. It is also possible to apply the compensation voltage to the first electrode 1 and the separation voltage to the second electrode 2. Even when the plus and minus of the compensation voltage are reversed, similar ion transmission can be achieved.

In step 407, the main measurement is performed. The ion to be measured is subjected to mass spectrometry measurement with the voltages being applied to the first electrode 1 and the second electrode 2 of the FAIMS, i.e., in a condition setting such that the ion to be measured is transmitted by the FAIMS but ions having other mobilities are not transmitted.

For the mass spectrometry measurement in the main measurement, known analysis/measurement methods may be used. Examples of the various mass spectrometry techniques that can be used include mass spectrometry that acquires a mass spectrum by m/z scanning; single ion monitoring (SIM) that monitors only the ion to be measured; tandem mass spectrometry (MS/MS) that acquires the mass spectrum of fragment ion by decomposing (dissociating) the ion to be measured; and multi reaction monitoring (MRM) that decomposes (dissociates) the ion to be measured and monitors only a specific fragment ion. With respect to one ion to be measured, the main measurement is implemented for a time designated by the user in advance (such as on the order of several milliseconds to several tens of seconds). After step 407, the process proceeds to step 408.

In step 408, it is determined whether the flow should be terminated. When the retention time (measurement time) reaches a predetermined set value, the analysis flow is terminated. If the retention time has not reached the set value, the process returns to step 401, and the analysis flow is repeated. In the present example, the set value indicates the time at which the sample separation in the LC ends and the sample measurement is terminated.

Figure 6:
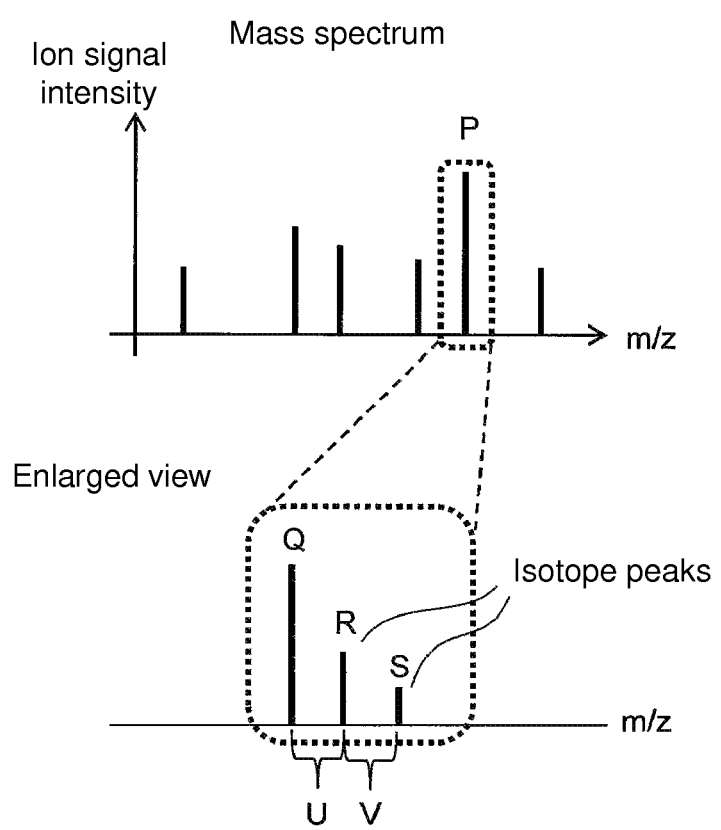
FIG. 6 illustrates diagrams for describing isotopes of a mass spectrum.

FIG. 6 illustrates a mass spectrum which is the mass spectrometry data displayed after ion detection, and an enlarged view of the peak of a certain one ion species. As illustrated in the enlarged view, the peak P may include a plurality of peaks (Q, R, S) arranged at regular intervals. These are referred to as isotope peaks. Ions having isotopes such as $^2$H (D) or $^{13}$C exhibit isotope peaks on the greater m/z value side, as illustrated in FIG. 6. When the peak list is created in step 403, it is preferable to handle the three peaks as one ion species. Thus, in the list, the three ions are displayed in one row. For the m/z value, the value of the leftmost peak Q or the peak having the maximum signal intensity is used. For the ion signal intensity, the signal intensity of only the leftmost peak Q or the maximum intensity peak may be used, or the sum of the three signal intensitys may be used.

A method of determining the ion charge amount (valence) from the mass spectrum peak will be described. For the valence determination, isotope peaks are used. Specifically, the valence is calculated from the peak interval (U, V) of adjacent peaks according to expression 1. When the peak interval is 1, the valence is 1; when 0.5, the valence is 2.

$$\text{Charge number}(z) = \frac{1}{\text{Peak interval}(m/z)} \quad \text{Expression 1}$$

The ionization method implemented in the ionization unit 12 may include an ionization method normally used in a mass spectrometer, such as electrospray ionization (ESI); atmospheric pressure chemical ionization (APCI); matrix-assisted laser desorption ionization (MALDI); desorption electrospray ionization (DESI); or atmospheric pressure photoionization (APPI).

In the present embodiment, a configuration combining the ion mobility separation unit 13 and the mass spectrometry unit 14 is used. The ion mobility separation unit 13 may include a FAIMS or a known ion mobility separation unit capable of separation similar to FAIMS. The ion mobility spectrometry may be performed in atmospheric pressure or in vacuum.

The mass spectrometry unit 14 includes a mass spectrometer, where normally detection is performed in vacuum. The mass spectrometer may include a known spectrometer such as, for example, an ion trap mass spectrometer such as a three-dimensional ion trap or a linear ion trap; a quadrupole mass spectrometer (Q filter); a triple quadrupole mass spectrometer; a time of flight mass spectrometer (TOF/MS); a Fourier transform ion cyclotron resonance mass spectrometer (FTICR); an orbitrap mass spectrometer; or a magnetic sector mass spectrometer. Other known mass spectrometers may also be used.

The details of the main measurement in step 407 will be described. The above-described mass spectrometer is used to monitor the ion to be measured. In mass spectrometry, a mass spectrum can be acquired by fixing the m/z of the ion transmitted by the FAIMS, and scanning the m/z of the ion transmitted by the mass spectrometer. Particularly, in all of the mass spectrometers mentioned above, a mass spectrum can be acquired by scanning m/z, for example. Alternatively, it is possible to measure only a specific ion by fixing the m/z of the ion transmitted by the FAIMS and further fixing the m/z transmitted by the mass spectrometer as well. As a result, measurement with a high S/N can be implemented. For example, single ion monitoring (SIM) analysis is performed using a quadrupole filter or a triple quadrupole mass spectrometer.

Meanwhile, in the case of tandem mass spectrometry (MS/MS) where the ion to be measured is decomposed and a fragment ion is monitored, a device for ion dissociation is required. An advantage of tandem mass spectrometry is that even when ions happened to have the same m/z, the ion species can be distinguished by the difference in ion structure. Specifically, when the original ion is decomposed and fragmented, the resultant pattern is different depending on the molecular ion structure, whereby the original ion can be distinguished. The tandem mass spectrometry enables separation of ions having similar m/z, and the S/N can also be increased. In the case of an ion trap, dissociation and analysis can be performed in the ion trap. Namely, after the ion is trapped, dissociation and mass spectrum acquisition can be implemented.

In the case of a triple quadrupole mass spectrometer, the ion of a certain m/z is transmitted by the FAIMS and a Q filter (Q1), and then ion dissociation is performed by a collision cell (Q2), and the transmitting m/z is fixed in a Q filter (Q3) for transmission, or the m/z is scanned. In this way, multi-reaction monitoring or a product scan can be performed. In another dissociation method, ion dissociation may be performed by a differential exhaust unit disposed between the FAIMS and a mass spectrometer. By feeding energy on the order of several 10 V to the ion and causing the ion to enter the differential exhaust unit, ion dissociation can be performed.

Ion dissociation may be implemented by various known ion dissociation methods, such as collision induced dissociation (CID); collision activated dissociation (CAD); infrared multiphoton dissociation (IRMPD); electron capture dissociation (ECD); or electron transfer dissociation (ETD).

In step 404, the ion to be measured may be determined by the following method. While the above-described method selected one peak, another method may select a plurality of upper ions arranged in the order of signal intensity. In this method, the frequency of mass spectrum acquisition in step 402 can be decreased, and a long time for the main measurement (step 407) can be ensured. With respect to an ion that has been measured for predetermined seconds or longer, it may also be effective to eliminate the ion from candidate ions to be measured. In this method, redundant measurement of the same ion can be prevented and instead another ion can be measured, whereby efficient measurement can be implemented.

In yet another method, an m/z value or charge amount (z) that has been designated by the user in advance via the input unit 20 may be registered in the database 19, and the designated ion may be preferentially selected as the ion to be measured. This is an effective method when the m/z of the ion to be measured is known in advance, as it enables the targeting of that ion for measurement.

In still another method, an ion having a previously designated m/z or charge amount (z) is eliminated from the ions to be measured. In this method, when there is a noise peak that keeps appearing on the mass spectrum, the noise can be eliminated. By these methods, efficiency can be increased, i.e., more ions can be measured per unit time, whereby high throughput analysis can be implemented.

While in the present embodiment the mass-to-charge ratio (m/z) and the charge amount (z) are used, because the mass m can be calculated from m/z and z, a method may use a combination of the mass m and the charge amount z.

Thus, according to the present embodiment, in the storage device of the control unit 18, there is stored a table associating the mass spectrometry result information (m/z, z) with the analysis condition (separation voltage and compensation voltage) relating to ion mobility separation. From the table, the analysis condition corresponding to the mass spectrometry result information (m/z, z) of the ion to be measured is read and determined as being the analysis condition for the ion to be measured. In this configuration, an analysis condition suitable for the ion to be measured can be determined in a short time, whereby the analysis process can be performed with increased efficiency. Further, because the analysis condition suitable for the ion to be measured is stored in the database 19 in advance, highly precise analysis can be implemented using the analysis condition.

Particularly, in the present embodiment, a corresponding analysis condition can be determined from the mass spectrometry result information of the ion to be measured. Thus, it is not necessary to measure finely at fine voltage pitches or widely in a wide range of voltages, as according to conventional art. Thus, the ion to be measured can be analyzed in a shorter measurement time. Accordingly, a high-throughput analysis process can be implemented.

A second example of the first embodiment will be described. In the example of FIG. 5, the database 19 is searched using the mass-to-charge ratio (m/z) and the charge amount (z). In the present embodiment, a method will be described whereby the LC retention time (elution time) is utilized for comparison with the database 19.

When there are ions of two types of different molecular species having the same m/z, their ion mobility differs because of different molecular structures, and therefore the FAIMS analysis condition may well be different. In the above example, the two types of ions are measured under the same analysis condition. On the other hand, in the present embodiment, the two types of molecular species having the same m/z are separated using the LC retention time. This utilizes the fact that the LC retention time differs due to different chemical properties. Accordingly, by adding the LC retention time as a search condition for the FAIMS analysis condition, it becomes possible to perform an operation under the optimum FAIMS analysis condition for each ion even when the ions have the same m/z.

Figure 7:
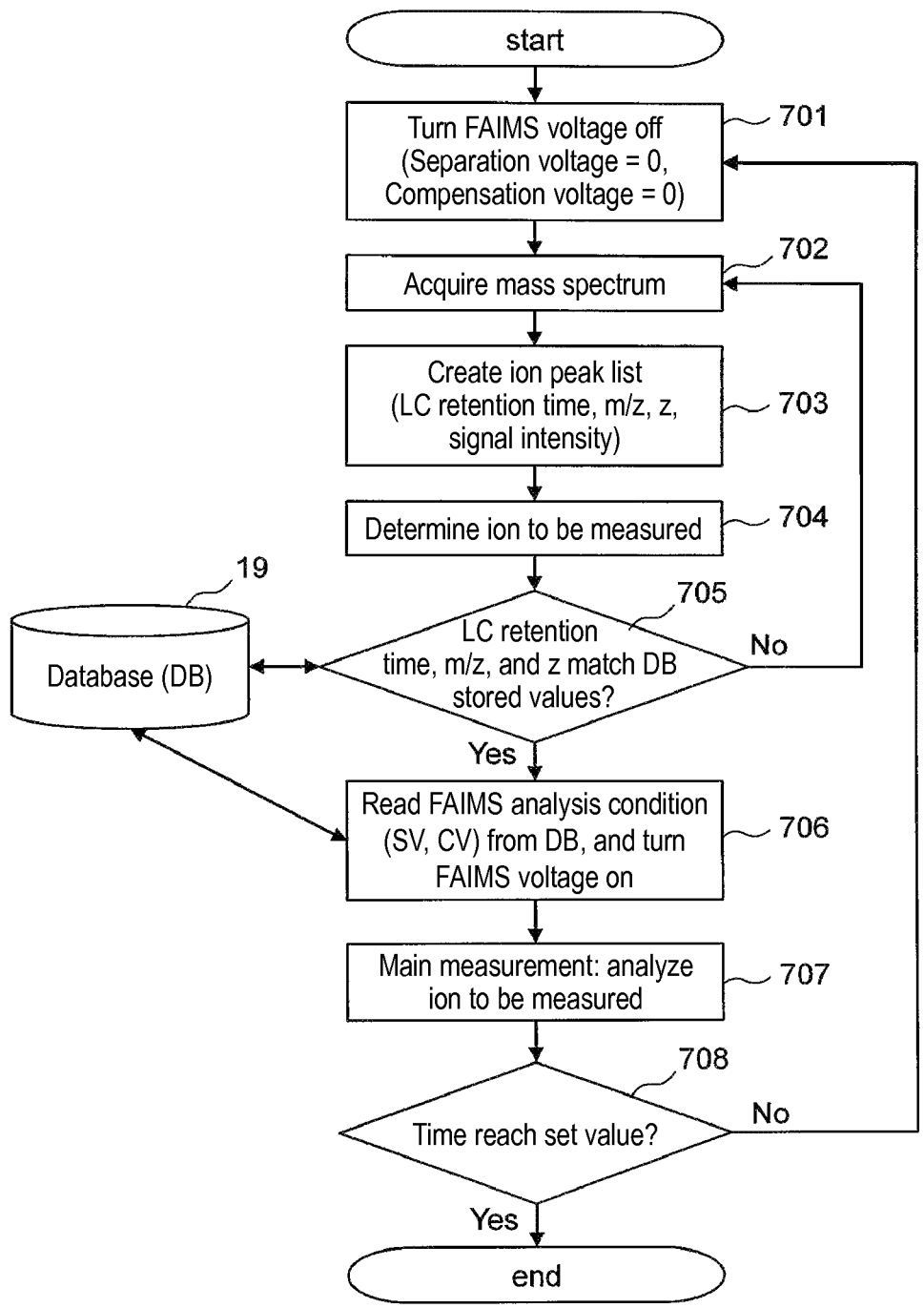
FIG. 7 illustrates another example of the measurement flow in the mass spectrometry system according to the first embodiment.
Figure 8A:
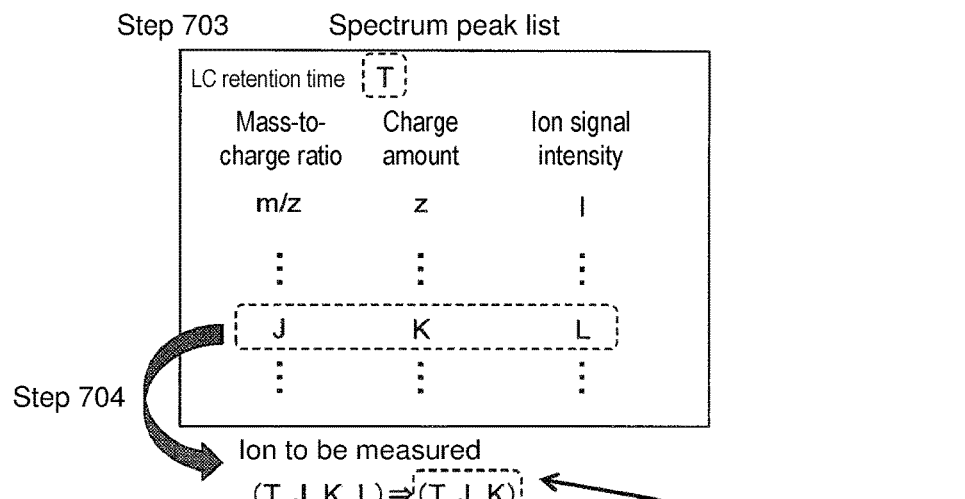
FIG. 8 illustrates diagrams for describing steps 703 to 706 of FIG. 7.
Figure 8B:
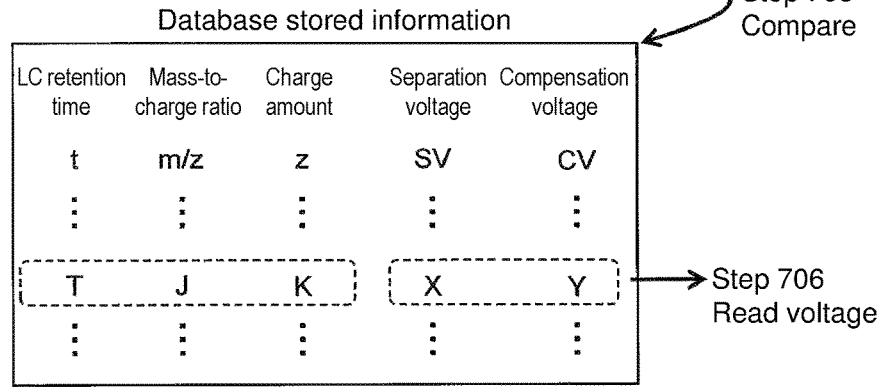

FIG. 7 illustrates the analysis flow according to the second example of the present embodiment. The flow of analysis is similar to the flow of FIG. 4. FIG. 8 illustrates diagrams for describing the flow of FIG. 7. In the following, with reference to FIG. 7 and FIG. 8, the exemplary analysis flow will be described, particularly with reference to portions different from FIG. 4.

As a feature of the present example, in step 703, when the ion peaks on the mass spectrum are determined to create the peak list, the information of the LC retention time (T) is added. As illustrated in FIG. 8A, the peak list including the three items of information of LC retention time, m/z, and z is created. Because the mass spectrum is acquired at each LC retention time, the peak list is created at each LC retention time.

In step 704, as described above, the ion with the highest signal intensity is selected as the ion to be measured, for example. Because the LC retention time information is added, the information of the ion to be measured includes LC retention time, m/z, z, and signal intensity; namely, (T, J, K, L). Because the ion signal intensity information (L) is not subsequently required, the information is deleted at this point in time, resulting in the information of the ion to be measured including (LC retention time, m/z, z); namely, (T, J, K).

In step 705, a comparison is made to determine whether the values (T, J, K) of the ion to be measured that have been obtained from the mass spectrum are registered in the database 19. If the difference between the ion to be measured (T, J, K) and the values stored in the database 19 is within a predetermined allowable range, it is determined that there is correspondence. The allowable value of the LC retention time may be on the order of several milliseconds to several seconds, and the allowable value of the m/z may be on the order of 0.001 Da to 1 Da. It is preferable that the allowable values are adapted to the respective analysis method of the respective mass spectrometry device.

According to the present example, in the storage device of the control unit 18, there is stored the table associating the mass spectrometry result information (LC retention time, m/z, z) with the analysis condition (separation voltage and compensation voltage) concerning ion mobility separation. The analysis condition corresponding to the mass spectrometry result information (LC retention time, m/z, z) of the ion to be measured is read from the table and determined as being the analysis condition for the ion to be measured. In this configuration, by adding the LC retention time, it becomes possible to determine the FAIMS analysis condition which is optimum for each ion even when ions have the same m/z.

A third example of the first embodiment will be described. As the mass spectrum data are acquired over many days, the mass axis (m/z) of the mass spectrum may be changed (displaced), although slightly, by changes in environment, such as temperature. As a result, data may be acquired as being those of a molecule of a different m/z even though the molecule is of the same molecular species. In this case, even if the analysis condition for that molecular species is stored in the database 19, it may be erroneously determined that the analysis condition is not stored. In such a case, it is necessary to correct the actually measured m/z value obtained by an analysis. In the present example, a method for correcting the m/z will be described. In the following description, the agent of the correction process is the control unit 18.

The mass axis (m/z) may be corrected by the following method, for example. Specifically, in the analysis sample or the LC delivery solvent, a known correction sample with a known m/z is mixed in advance, and the mass axis is corrected using the peak m/z of the correction sample. The correction sample may be of one type; however, by putting in two or more types, more accurate mass correction can be performed. For example, by putting in a correction sample with a small m/z and another with a large m/z, it becomes possible to accurately correct a wide m/z range of the mass axis.

FIG. 9 illustrates diagrams for describing the method for correcting m/z. FIG. 9(A) illustrates a drawing on a mass spectrum of theoretical values of two types of correction samples that have been mixed. In reality, various sample peaks including the peaks of the correction samples appear, as illustrated in FIG. 9(B). Among these, the correction sample peaks are found, and actually measured values of the peaks (a, b) are corrected to the m/z of the theoretical values. In the correction method according to the present example, a function (such as a line or curve) of the m/z of the theoretical values with respect to the actually measured m/z of the correction samples is determined, and all of the peaks derived from the samples are corrected according to the function. FIG. 9(C) illustrates the result of correction of the actually measured values of the peaks of (B) according to the obtained function. Other known correction methods may be employed.

According to the correction process of the present example, even when the mass axis (m/z) of the mass spectrum is changed by a change in environment, such as temperature, the analysis condition can be determined by using the same database 19.

A fourth example of the first embodiment will be described. As in m/z, the LC retention time may also be changed over time or by environment. Accordingly, it is necessary to correct the LC retention time obtained by a measurement. In the present example, a method for correcting the LC retention time will be described. In the following description, the agent of the correction process is the control unit 18.

The LC retention time correction method, as in the case of m/z correction, includes mixing a correction sample with a known LC retention time in a sample in advance, and then correcting the mass axis (m/z) by using the retention time of the peak of the correction sample. Specifically, a correction sample with a known retention time is mixed in the analysis sample or the LC delivery solvent in advance, and the mass axis is corrected using the retention time of the peak of the correction sample. While the correction sample may be of one type, by putting in two or more types, more accurate correction can be implemented. For example, by putting in a correction sample of a small retention time and another of a large retention time, a wide range of retention time can be accurately corrected.

FIG. 10 illustrates diagrams for describing the LC retention time correcting method. FIG. 10(A) illustrates a drawing on a chromatogram of the theoretical values of two types of correction samples that have been mixed. In reality, the chromatogram of all ions is drawn where the peaks of various samples, including the peaks of the correction samples, appear, as illustrated in FIG. 10(B). Among the peaks, the peaks of the correction samples are found, and the actually measured values of the peaks (c, d) are corrected to the retention times of the theoretical values. In the correction method according to the present embodiment, a function (such as a line or curve) of the retention times of the theoretical values with respect to the actually measured retention times of the correction samples is determined, and all of the peaks derived from the samples are corrected according to the function. FIG. 10(C) illustrates the result of correction of the actually measured values of the peaks shown in (B) according to the determined function. Other known correction methods may be employed.

Apart from the displacement due to a change in environment, such as temperature, when the type of the column used in the LC (the column for molecular sample adsorption or trapping) is changed, the LC retention time may be varied even for the same molecular species. Thus, because the LC retention time varies depending on the column type, a mismatch with the information stored in the database 19 may result. However, when the length of the column is changed, if the LC retention time is simply proportional to the column length or can be drawn as a function of the column length, the database 19 of the same FAIMS analysis condition can be used. For example, the LC retention time can be corrected according to the function of the column length.

In the configuration of the present example, the database 19 can be commonly utilized even when the column type is changed. Accordingly, it is not necessary to retain a plurality of databases for respective columns, whereby the use of resources in the control unit 18 can be decreased.

In liquid separation using an LC, LC/MS analysis may be performed while the ratio of two types of delivery solvents is changed in time. This is because, by changing the composition of the solvent, the retention force that holds the sample on the column is changed, whereby the sample is eluted. When eluted, the sample is ionized and subjected to mass spectrometry.

Figure 11A:
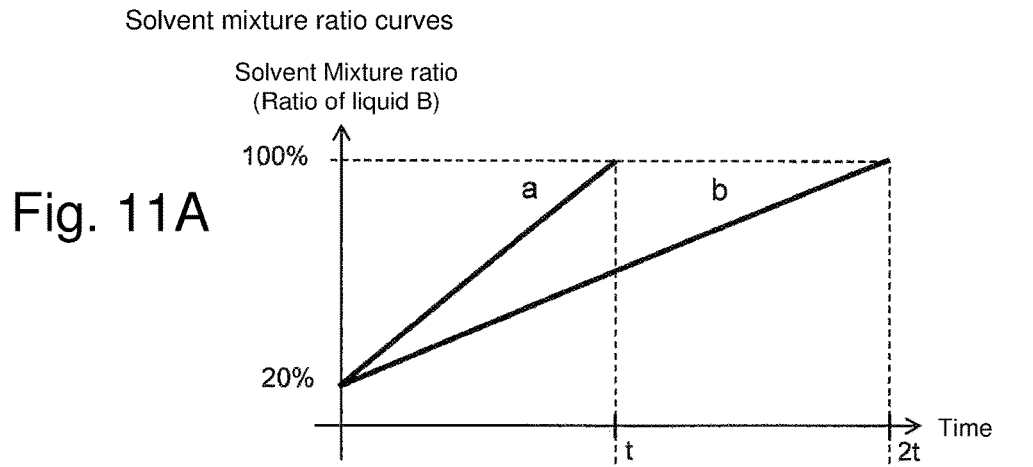
FIG. 11 illustrates diagrams for describing a relationship between a delivery solvent mixture ratio and chromatograms.

FIG. 11(A) illustrates changes in the delivery solvent mixture ratio used in the LC with respect to time. At time 0, liquid A mainly including water (+buffer) is 80%, and liquid B mainly including methanol or acetonitrile is 20%. Over time, the ratio of liquid B is gradually increased, so that the ratio of liquid B becomes 100% at time t for line a and at time 2t for line b, whereupon the analysis ends. The time t is the set value in step 408 or 708 in the flow of FIG. 4 or FIG. 7.

Figure 11B:
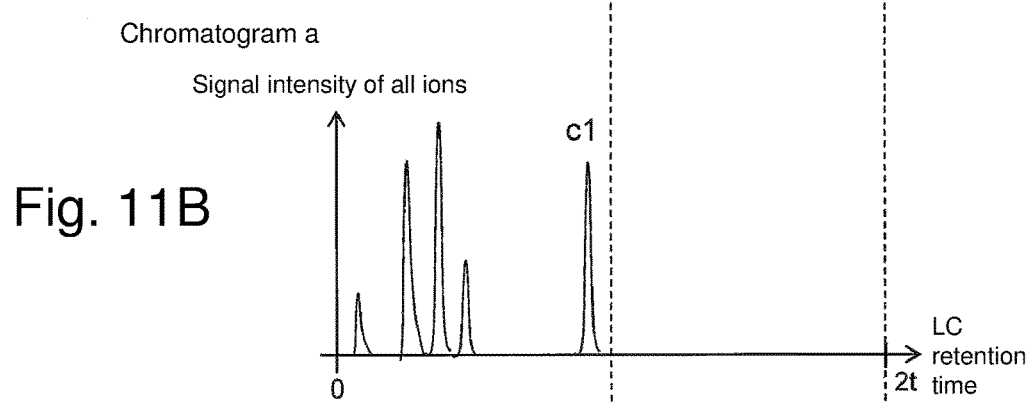
Figure 11C:
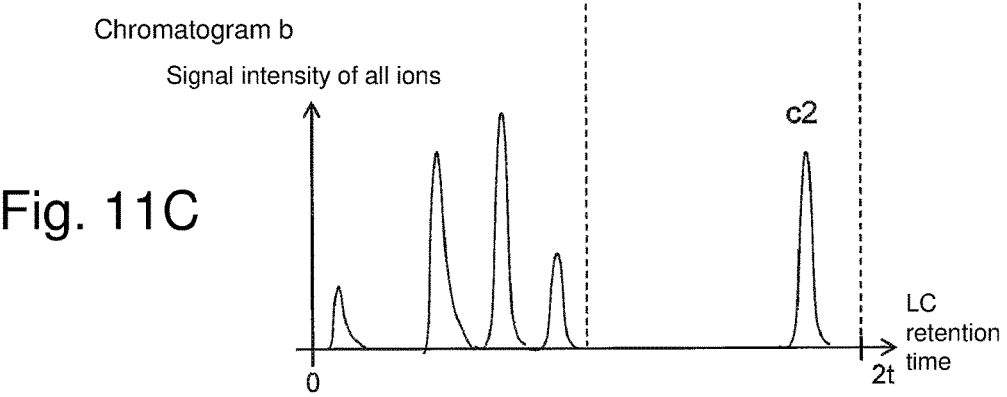

FIG. 11(B) and FIG. 11(C) respectively illustrate chromatograms obtained in correspondence to the changes a and b in the mixture ratio of the solvent (liquid B) in FIG. 11(A). When the solvent mixture ratio is changed over time t, as for line a, samples are detected as shown in chromatogram a (FIG. 11(B)).

On the other hand, when the solvent mixture ratio is changed over time 2t, as for line b, the peaks are detected over twice the time, as shown in chromatogram b. In this case, the peak of "c1" in FIG. 11(B) and the peak of "c2" in FIG. 11(C) are of the same molecular species. Thus, by changing the solvent mixture ratio, the LC retention time becomes different. Accordingly, when the LC retention time is included in the database 19, it is necessary to use a different database when the mixture ratio is changed. In the following, a method will be described whereby the same database can be utilized even when the mixture ratio is changed.

In the present example, a method of correcting the LC retention time when the solvent mixture ratio with respect to time is indicated by lines with different slopes, as shown in FIG. 11(A), will be described. In the database 19, the LC retention time acquired with line a is registered. In this case, the LC retention time for chromatogram b the data of which have been newly acquired with line b is corrected. In the case of the example of FIG. 11(A), the slope of line a and line b is calculated. Line a has slope 2N, and line b has slope N. Thus, the LC retention time of the data of chromatogram b is corrected by the slope ratio, i.e., by a factor of ½. This correction process is possible when the mixture ratio lines are of the same type of function. Similar correction can be performed using functions other than the above-described lines (linear functions), such as polynomial functions including quadratic functions, exponential functions, and logarithmic functions.

According to the configuration of the present example, even when LC/MS analysis is performed while the ratio of two types of delivery solvent is changed in time, the database 19 can be commonly utilized by correcting the LC retention time. Thus, it is not necessary to provide a plurality of databases, whereby the use of resources in the control unit 18 can be decreased.

A fifth example of the first embodiment will be described. In the example of FIG. 4, the mass spectrometry time of the main measurement in the step 407 is a predetermined time. In the following example, a method will be described whereby the mass spectrometry time of the main measurement is determined in real-time based on the acquired mass spectrum data.

Figure 12:
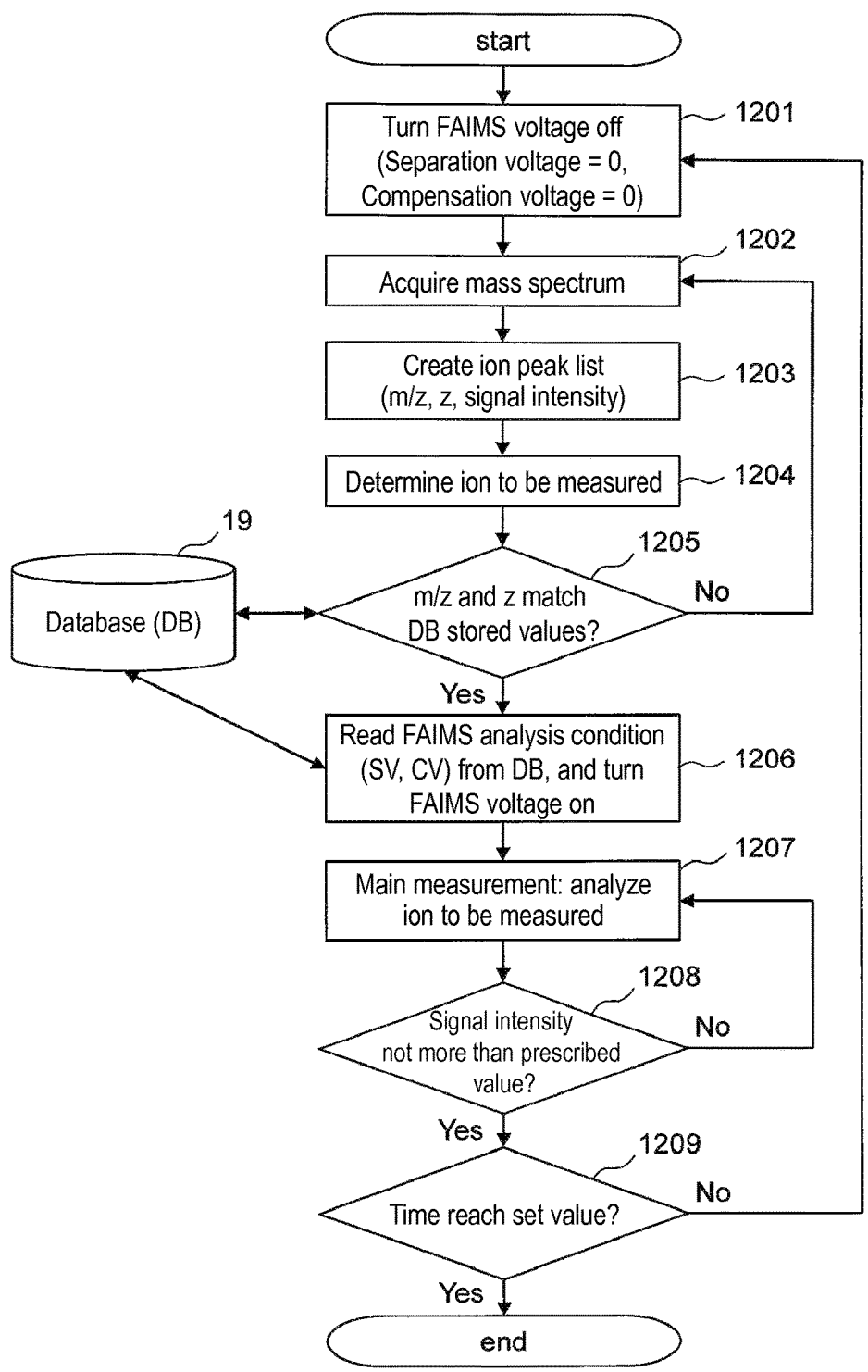
FIG. 12 illustrates another example of the measurement flow of the mass spectrometry system according to the first embodiment.

FIG. 12 illustrates the flow of analysis in the fifth example of the first embodiment. The analysis flow is similar to the flow of FIG. 4. Description of steps 1201 to 1207 and 1209 of FIG. 12 will be omitted as they are similar to steps 401 to 408 of FIG. 4. The difference from FIG. 4 is that there is additional step 1208. In step 1208, it is determined whether the signal intensity of the ion to be measured is not more than a certain prescribed value.

When the ion signal intensity became a certain prescribed value or less, the process proceeds to step 1209 (Yes in step 1209), and the measurement of the ion to be measured is terminated. On the other hand, if the signal intensity of the ion to be measured is the prescribed value or more; namely, if the ion to be measured keeps being detected, the process returns to step 1207 (No in step 1208), and the main measurement is continued.

Figure 13:
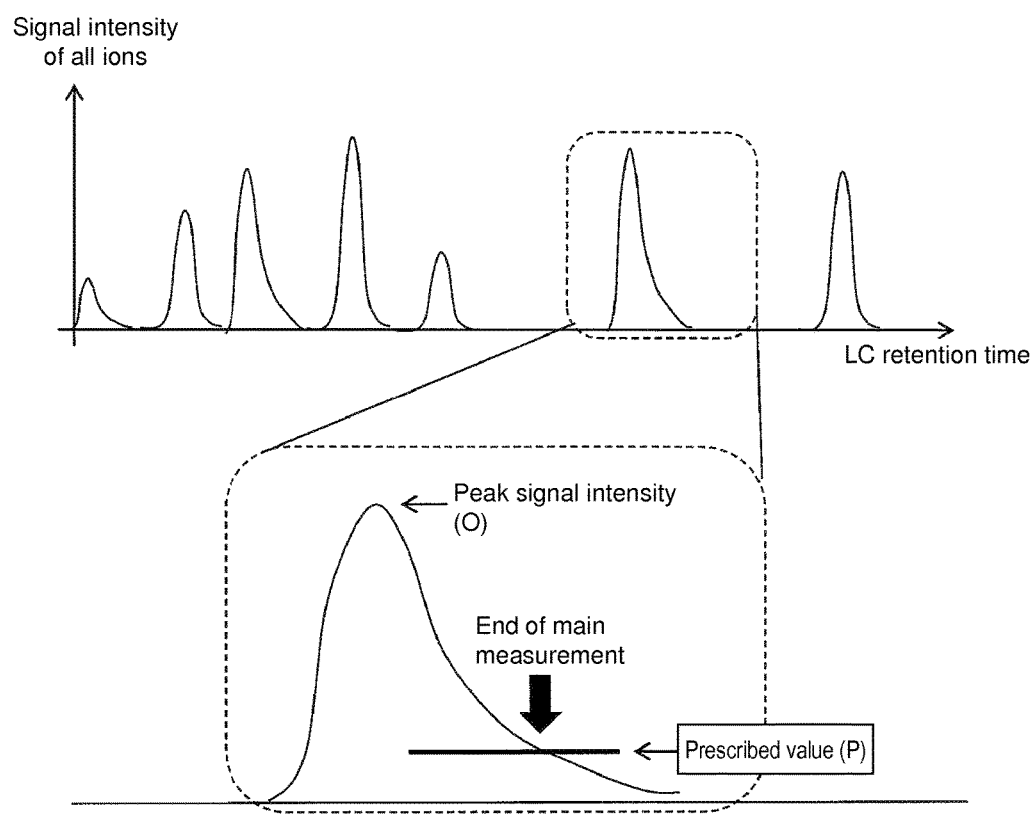
FIG. 13 illustrates diagrams for describing a termination condition for step 1208 in FIG. 12.

FIG. 13 is a diagram for describing the determination in step 1208. For example, as illustrated in FIG. 13, as the data of the signal intensity of the ion to be measured and the analysis time, a mass chromatogram with a peak signal intensity O is obtained by measurement. In this case, when the signal intensity drops to the line of a prescribed value (P) or below, the main measurement is terminated. The prescribed value P is a previously set value, or a value designated by the user via the input unit 20. Typically, the prescribed value P may be a value within a range of 1% to 80% of the peak signal intensity O (P/O=0.01 to 0.8).

In this configuration, the mass spectrometry time of the main measurement can be determined in real-time based on the acquired mass spectrum data. By thus determining the mass spectrometry time in real-time, it becomes possible to transition to the analysis of the next ion to be measured immediately after the end of the analysis of a certain ion to be measured. For example, when the ions to be measured overlap with one another during an actual analysis, a decrease in the analysis time for the next ion to be measured can be prevented, whereby the analysis of a plurality of ions to be measured can be efficiently performed.

A sixth example of the first embodiment will be described. According to the method of the foregoing examples, one ion to be measured is selected from the mass spectrum. However, according to another method, a plurality of (N) ions to be measured may be selected and determined.

Figure 14:
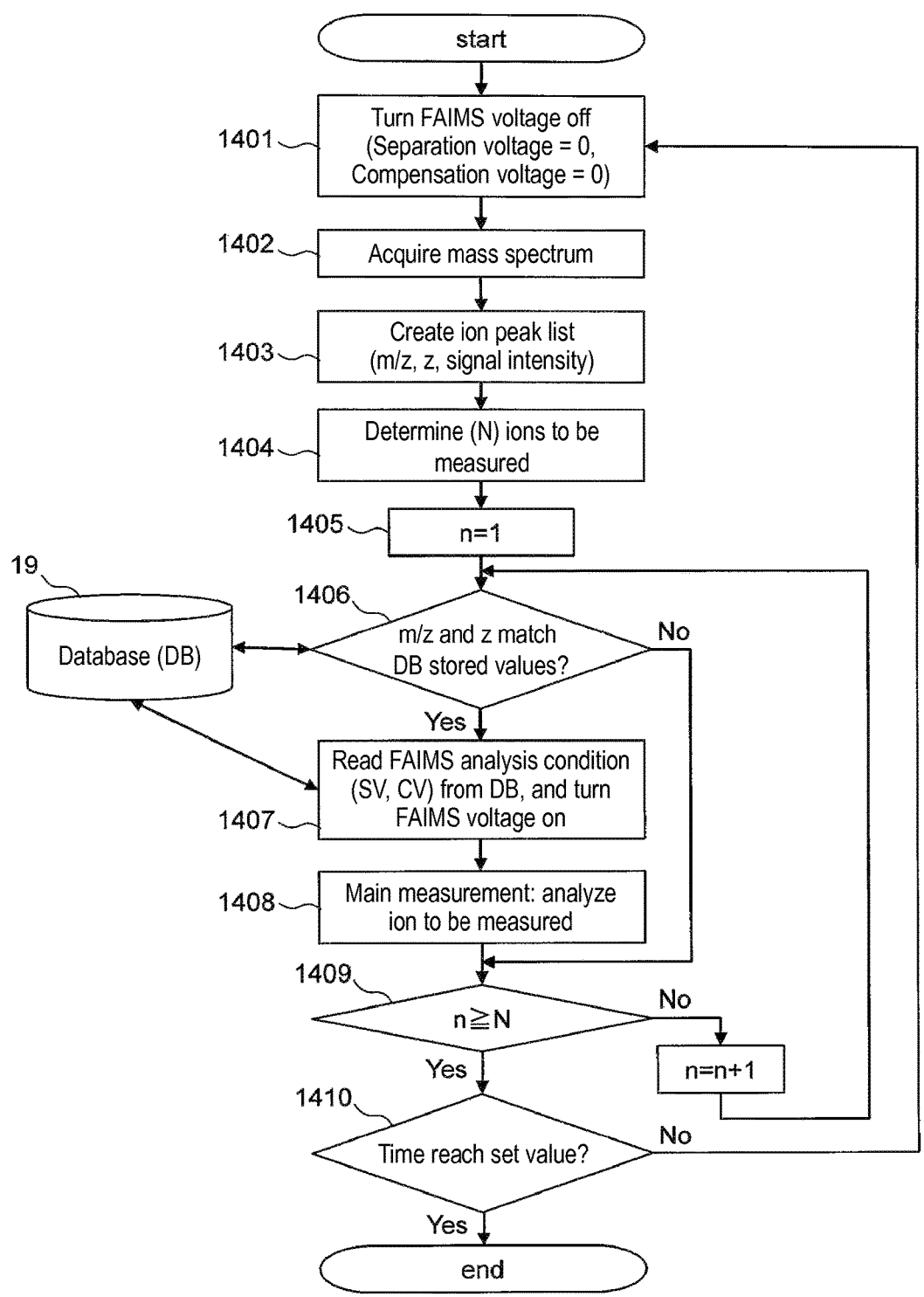
FIG. 14 illustrates another example of the measurement flow of the mass spectrometry system according to the first embodiment.

FIG. 14 illustrates the flow of analysis according to the present embodiment. The analysis flow is similar to the flow of FIG. 4. Description of steps 1401 to 1403, 1406 to 1408, and 1410 of FIG. 14 will be omitted as they are similar to steps 401 to 403 and 405 to 408 of FIG. 4. In the following, particularly the different portions from FIG. 4 (steps 1404, 1405, 1409) will be described.

In step 1404, N ions to be measured are determined at once (in the following example, the selected number N=3). While three ions to be measured are selected in the example, a similar measurement method may be implemented as long as the selected number of ions is two or more. The number of selected ions (selected number N) may be a previously set value or a value designated by the user via the input unit 20.

In step 1404, the three ions to be measured are selected in the order of decreasing ion signal intensity (N=3). In another method, three peaks with high S/N (signal to noise ratio) may be selected. In other methods, as a limiting condition for the selection of the ions to be measured, only ions with a certain charge amount z, or only ions in a certain m/z range may be selected as the object of measurement. Further, when the m/z of the target ion is known, the object of measurement may be restricted to around the m/z of the target ion, whereby target ion measurement can be efficiently implemented. In addition, a method may be employed whereby the ions that have already been measured are eliminated from the object of measurement. In this way, redundant measurement of the same ion can be avoided. While the number of selected ions may differ from that of steps 404 and 704 described above, the determination method may be similar.

In step 1405, initially, of the three ions to be measured, the first ion to be measured is set; namely, n=1. In the next step 1406, it is confirmed whether the information of the first ion to be measured matches values stored in the database 19. If the information does not match the values stored in the database 19, i.e., if there is no analysis condition information in the database 19, the process proceeds to step 1409 without performing the main measurement.

On the other hand, if in step 1406 the information of the first ion to be measured matches the database 19, i.e., if there is analysis condition information in the database 19, the process proceeds to steps 1407 and 1408 and the main measurement is performed. After the main measurement, the process proceeds to step 1409.

In step 1409, it is determined whether steps 1406 to 1408 are to be repeated. In the present example, at the point in time of N=3, i.e., at the end of the measurement of the three ions to be measured (Yes in step 1409), the process proceeds to step 1410. If at the end of measurement of the first ion (n=1) or the second ion (n=2) (No in step 1409), the process returns to step 1406. In other words, the flow is repeated until n is 3 and the measurement of the selected three ions is completed.

According to the configuration of the present example, the frequency of mass spectrometry data acquisition in step 1402 is decreased. As a result, the time for the main measurement is increased, whereby the throughput of analysis is increased and efficient analysis becomes possible.

Second Embodiment

A second embodiment will be described. In the present embodiment, a method will be described whereby, when the information of the ion to be measured is not stored in the database 19; namely, when there is no FAIMS analysis condition in the database 19, the FAIMS analysis condition for that ion is created.

Figure 15A:
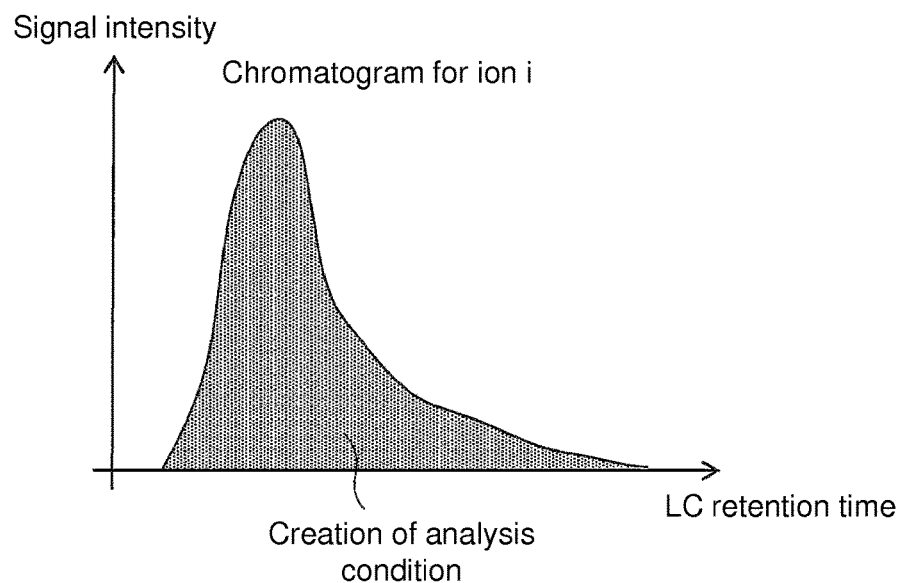
FIG. 15A illustrates a diagram for describing a chromatogram obtained by a first analysis according to a second embodiment.

In the present embodiment, a method will be described whereby analysis condition creation and storage in the database 19 are performed in the first LC/MS analysis and the main measurement is performed in the second or a subsequent LC/MS analysis. FIG. 15A illustrates a chromatogram of an ion i as the object of measurement in the first LC/MS analysis. In the first LC/MS analysis, as illustrated in FIG. 15A, only the creation of the FAIMS analysis condition is performed while the ion i is being detected.

Figure 15B:
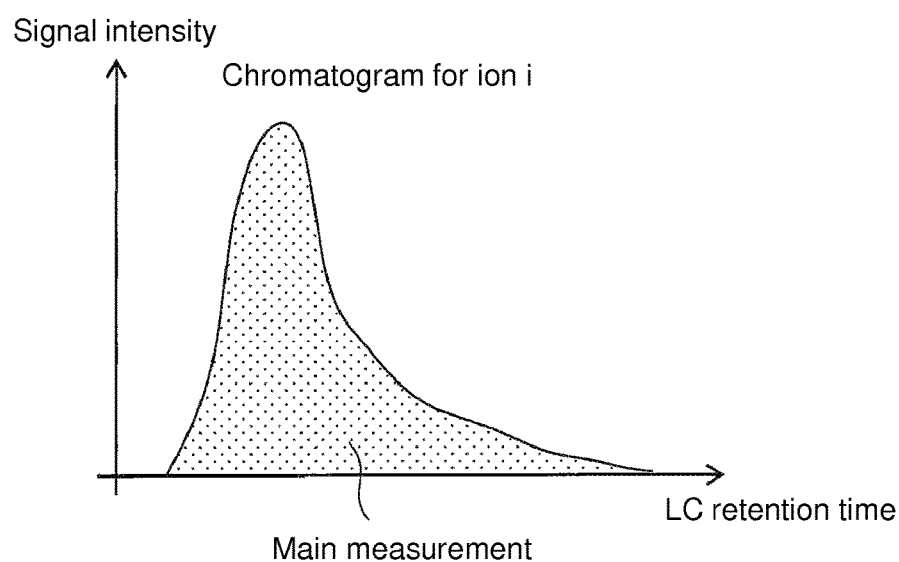
FIG. 15B illustrates a diagram for describing a chromatogram obtained by the second or a subsequent analysis according to the second embodiment.

FIG. 15B illustrates a chromatogram of the ion i as the object of measurement in the second or a subsequent LC/MS analysis. In the second or a subsequent LC/MS analysis, all of the analysis time can be used for the main measurement. Thus, in the second or a subsequent LC/MS analysis, almost the entire amount of the ion i can be measured by the main measurement. Accordingly, the present embodiment, being capable of accurately measuring the ion amount, is suitable for quantitative analysis.

Figure 16A:
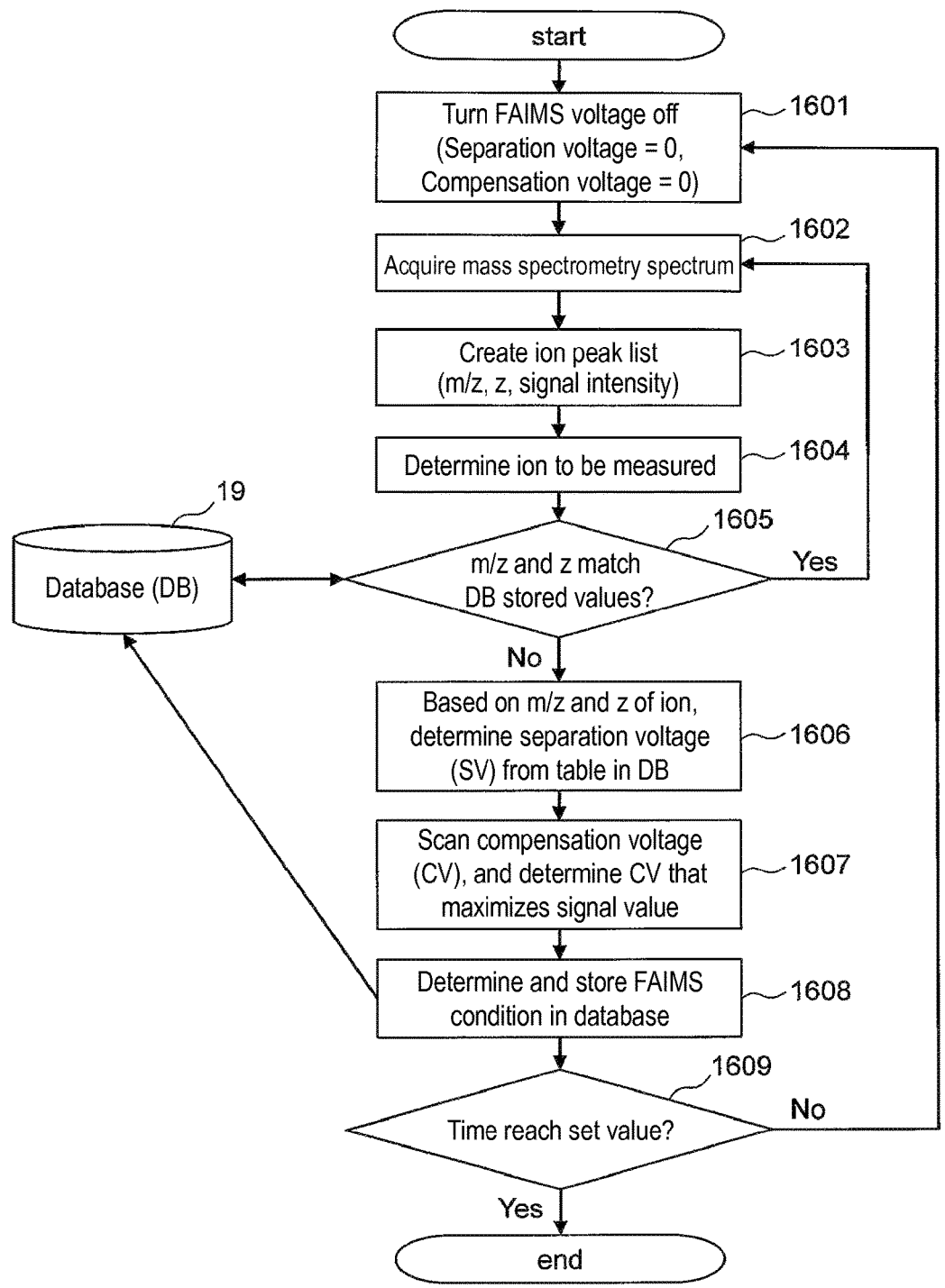
FIG. 16A illustrates a flow for creating an FAIMS analysis condition in the first LC/MS analysis.

FIG. 16A illustrates a flow for creating the FAIMS analysis condition in the first LC/MS analysis. The agent of the following process is the control unit 18. The control unit 18, while controlling the ion mobility separation unit 13, the mass spectrometry unit 14, and the ion detection unit 15, executes the following process. Description of steps 1601 to 1604 will be omitted as they are similar to steps 401 to 404 of FIG. 4.

In step 1605, a comparison is made to determine whether the ion to be measured is registered in the database 19. If the ion to be measured matches stored values in the database 19; namely, if the FAIMS analysis condition is already registered in the database 19, the result of the determination is Yes, and the process returns to step 1602. Then, a mass spectrometry spectrum is again acquired and searched for another ion to be measured.

In step 1605, if the ion to be measured does not match the stored values in the database 19; namely, if the FAIMS analysis condition is not registered in the database 19, the result of the determination is No, and the process proceeds to step 1606. In the subsequent steps 1606 to 1608, FAIMS analysis condition search, determination, and storage in the database 19 are performed.

In step 1606, the FAIMS separation voltage (SV) is determined from the information of the ion to be measured (m/z, z). The separation voltage, which is a high frequency voltage, depends on the weight of the ion or its m/z. Generally, when an ion is passed in an electric field of a certain strength, the acceleration a on the ion due to the electric field is expressed by the mass m and the charge amount z according to the following relational expression:

$$\text{Acceleration } a \propto \frac{\text{Charge amount } z \times \text{Electric field } E}{\text{Mass } m} \quad \text{Expression 2}$$

Thus, the acceleration a is inversely proportional to the mass m, so that under a certain electric field, the acceleration on an ion with a large mass due to the electric field is small, while the acceleration on an ion with a small mass is large. For example, the small-mass ion may collide with an electrode due to the influence of the electric field, making it difficult to perform mass spectrometry. Accordingly, in an FAIMS too, it is necessary to vary the electric field, i.e., the separation voltage, depending on the mass of the ion, i.e., m/z, for optimization. In a separation voltage determination method, a separation voltage table (second information) stored in the database 19 in advance describing the relationship between m/z and separation voltage is used.

Figure 17A:
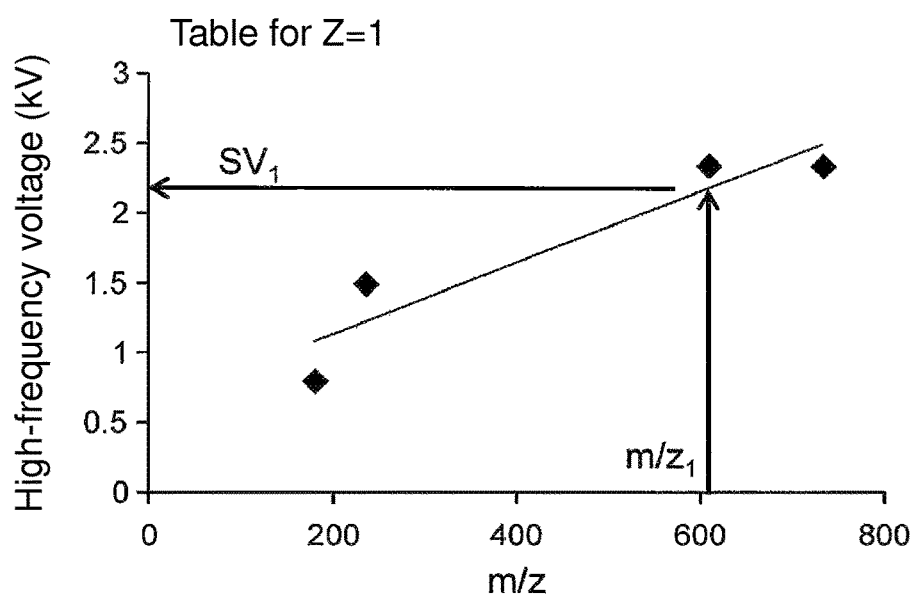
FIG. 17A illustrates a diagram for describing a separation voltage determination method for step 1606 of FIG. 16A.

FIG. 17A is a diagram for describing the content of the separation voltage table. In the separation voltage table, there is stored information associating the mass-to-charge ratio (m/z) with the separation voltage. As described above, it is preferable to apply the electric field strength, i.e., the separation voltage, in accordance with m/z. For example, when the acceleration of expression 2 is to be made constant, it is necessary to make m/z and the electric field (separation voltage) linear. Namely, as illustrated in FIG. 17A, the relationship (separation voltage table) between m/z and separation voltage is drawn by a linear function. The separation voltage table describes the relationship between m/z and separation voltage in advance, so that the optimum separation voltage is uniquely determined by the m/z of the ion to be measured. In the example of FIG. 17A, the separation voltage for the ion to be measured is determined to be the separation voltage $SV_1$ associated with $m/z_1$.

In the present example, the separation voltage table is linear. However, the relationship between m/z and separation voltage may be configured by a line having two different slopes for each range of m/z. The relationship between m/z and separation voltage may include a curve or functions such as multi-order functions and exponential functions.

Because the separation voltage table depends on the ion charge amount (z), there may be a separate table for each charge amount. This is because, as indicated by expression 2, the acceleration a to which an ion is subject is inversely proportional to the mass m and proportional to the charge z.

It is also possible to create a separation voltage table. In a method for creating the separation voltage table, several separation voltage points are set, and the compensation voltage is scanned at each separation voltage so as to acquire signal intensity data. The compensation voltage is used where the signal intensity is at a maximum. By thus acquiring the ion signal intensity at each separation voltage, an optimum separation voltage can be determined from the two items of signal intensity and FAIMS resolution (=compensation voltage value/half value width). The optimum separation voltage should have high signal intensity and high resolution. It is also preferable to vary the separation voltage table in accordance with the temperature of the ion mobility separation unit 13. This is because the temperature of gas on the ion trajectory also varies depending on the FAIMS temperature and therefore the ion mobility changes. For example, different separation voltage tables are used for 100° C., 200° C., and 300° C. Other than temperature, the separation voltage table may be changed depending on environment, such as pressure and the flow velocity of gas flowing in the FAIMS.

In step 1607, the compensation voltage (CV) is determined under the condition of the separation voltage determined in step 1606. Specifically, the control unit 18, while applying the separation voltage determined in step 1606, scans a plurality of compensation voltages with respect to the ion to be measured, and determines a compensation voltage on the basis of the ion signal intensity at the plurality of compensation voltages.

The compensation voltage is determined as an optimum voltage by scanning a wide range. The compensation voltage scan range is −10 V to 10 V, −50 V to 50 V, or −100 V to 100 V, for example. The voltage scan pitch is 0.01V, 0.05V, 0.1V, 0.2V, 0.3V, or 0.5V, for example, or it may be other pitches. In one method of determining an optimum voltage of the compensation voltage, a compensation voltage such that the signal intensity of the ion to be measured is maximized is determined.

Figure 17B:
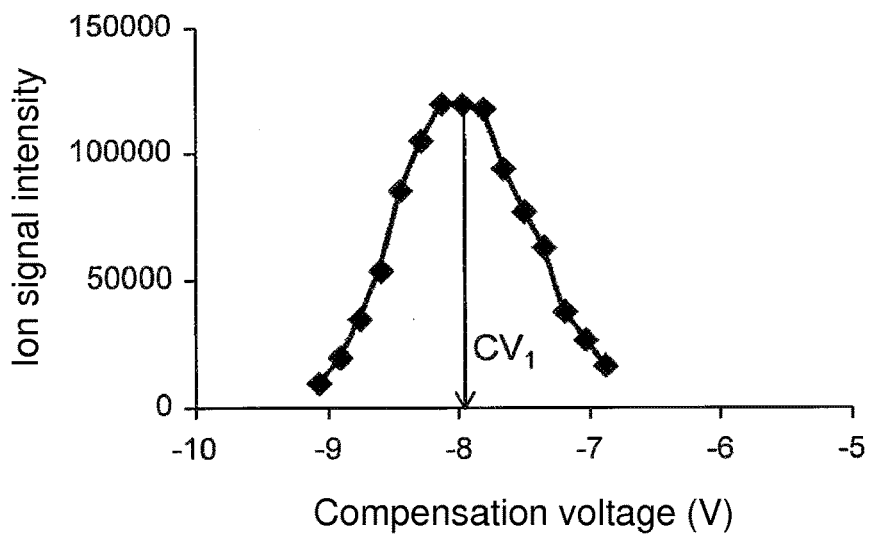
FIG. 17B illustrates a diagram for describing a compensation voltage determination method for step 1607 of FIG. 16A.

FIG. 17B is a diagram for describing compensation voltage determination. As illustrated in FIG. 17B, in a predetermined compensation voltage scan range, the signal intensity of the ion to be measured is measured at certain pitches. In the example of FIG. 17B, the compensation voltage $CV_1$ is determined at which the signal intensity of the ion to be measured is maximized.

In another method, a signal intensity curve with respect to an obtained compensation voltage may be approximated by a Gaussian function, a Poisson distribution, or other function, and a compensation voltage as a maximum value of the function may be determined to provide the optimum voltage.

In step 1608, information of the separation voltage $SV_1$ and the compensation voltage $CV_1$ is stored in the database 19. For example, a set of information (m/z, z, $SV_1$, $CV_1$) is stored in the database 19. The LC retention time may also be included. The stored data are used for the main measurement in the second or a subsequent LC/MS analysis.

Figure 16B:
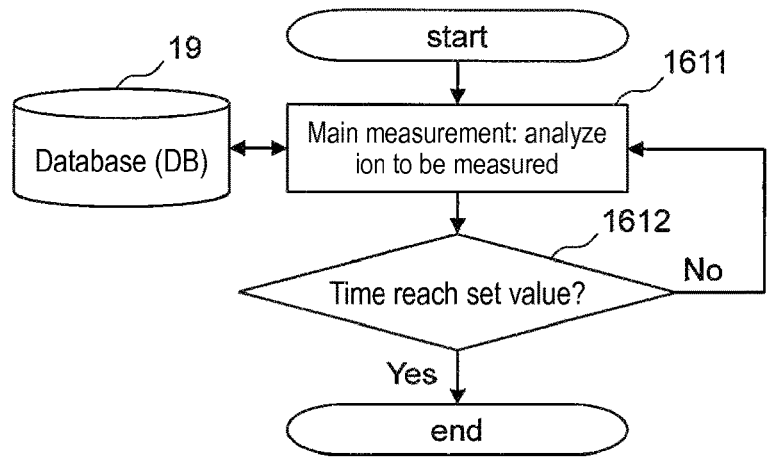
FIG. 16B illustrates a flow of the second or a subsequent LC/MS analysis.

The second or a subsequent LC analysis will be described. FIG. 16B illustrates the flow of the second or a subsequent LC/MS analysis. In the second or a subsequent LC/MS analysis, the main measurement is performed with respect to one or a plurality of ions in the database 19 created for the first time.

In step 1611, the FAIMS analysis condition is read from the database 19 with respect to a certain ion to be measured. Under the analysis condition acquired from the database 19, voltages are applied to the first electrode 1 and the second electrode 2 of the FAIMS, and the main measurement is performed. For example, in the first LC/MS analysis, information of the LC retention time of the ion to be measured is recorded, and when it is the LC retention time for the ion to be measured, the main measurement for the ion is repeatedly performed. The main measurement for the ion is repeatedly performed until the signal intensity becomes a certain prescribed value or lower, or until the LC retention time for another ion to be measured comes.

In step 1612, it is determined whether the analysis flow should be terminated. When the retention time (measurement time) reaches a predetermined set value, the analysis flow is terminated.

According to the present embodiment, if the mass spectrometry result information (m/z, z) of the ion to be measured does not match the mass spectrometry result information (m/z, z) in the database 19, namely, if the analysis condition (separation voltage and compensation voltage) for the ion to be measured is not stored in the database 19, the analysis condition for the ion to be measured can be determined and stored in the database 19. Particularly, the analysis condition is stored in the database 19 during the first LC/MS analysis, and the main measurement is performed during the second or a subsequent LC/MC analysis. Thus, in the second or a subsequent LC/MS analysis, almost the entire ion amount of the ion to be measured can be measured.

By using the separation voltage table associating the mass-to-charge ratio (m/z) with the separation voltage, the optimum separation voltage for the ion to be measured can be uniquely determined. Further, because the compensation voltage is scanned in a wide range with the separation voltage being applied, the optimum compensation voltage for the ion to be measured can be determined.

Figure 19:
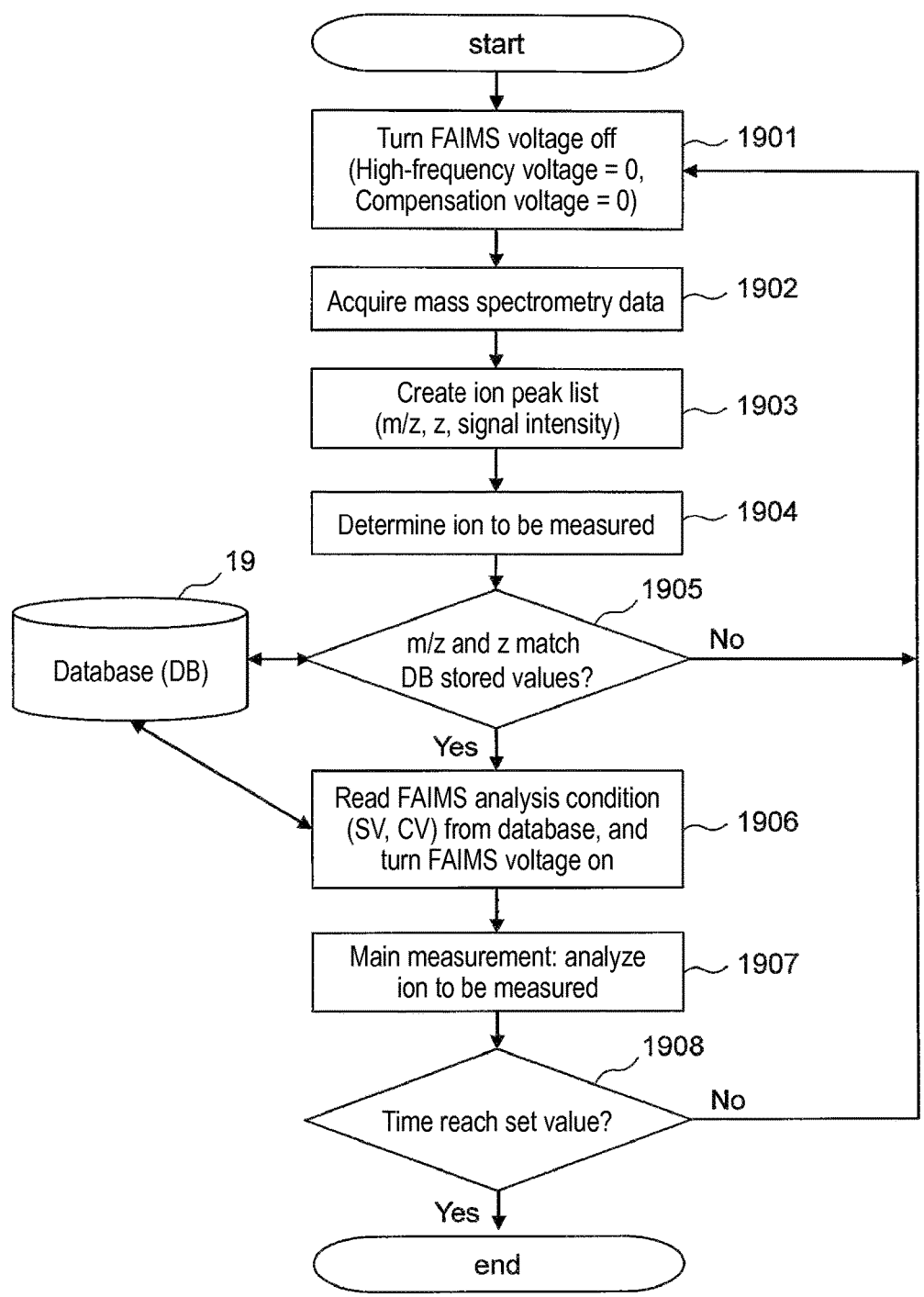
FIG. 19 illustrates another example of the flow of the second or a subsequent LC/MS analysis according to the second embodiment.

FIG. 19 illustrates another flow of the second or a subsequent LC/MS analysis. In this example, mass spectrum data are acquired, and when the ion to be measured is detected, the main measurement is performed. Description of steps 1901 to 1903 and steps 1905 to 1908 of FIG. 19 will be omitted as they are similar to steps 401 to 403 and steps 405 to 408 of FIG. 4.

In step 1904, it is determined whether an ion to be measured has been detected using the mass spectrum data acquired in steps 1902 and 1903. In step 1905, if the analysis condition for the ion to be measured is present in the database, the process proceeds to step 1905 to perform the main measurement for the ion (Yes in 1905). On the other hand, if not present, the flow returns to step 1901. In the present example, the main measurement is performed after the detection of the ion is confirmed. Thus, the process can transition to the measurement of another ion to be measured if a certain ion to be measured is not detected. Accordingly, a large number of ions can be analyzed efficiently.

Third Embodiment

A third embodiment will be described. In the present embodiment, a method will be described whereby the creation of the FAIMS analysis condition and the main measurement under the analysis condition are simultaneously implemented within a single LC/MS analysis.

Figure 18A:
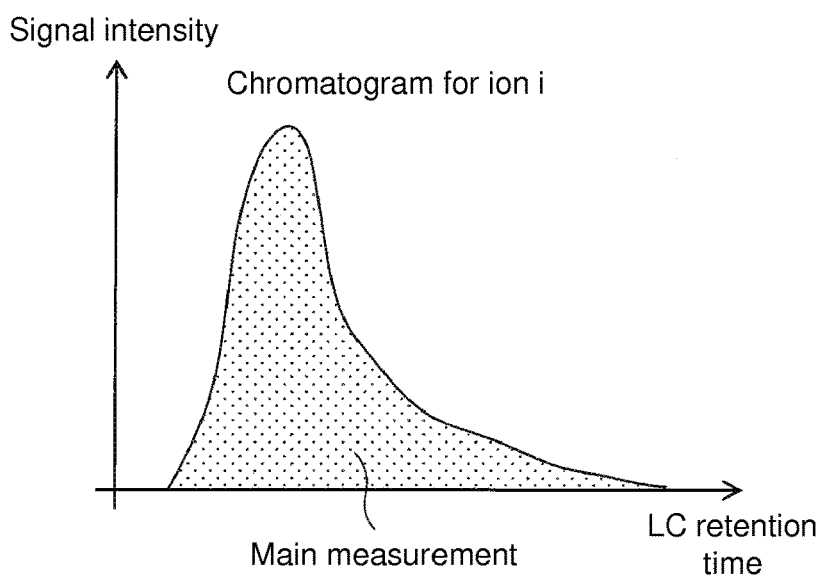
FIG. 18A illustrates a diagram for describing a chromatogram according to the second embodiment.
Figure 18B:
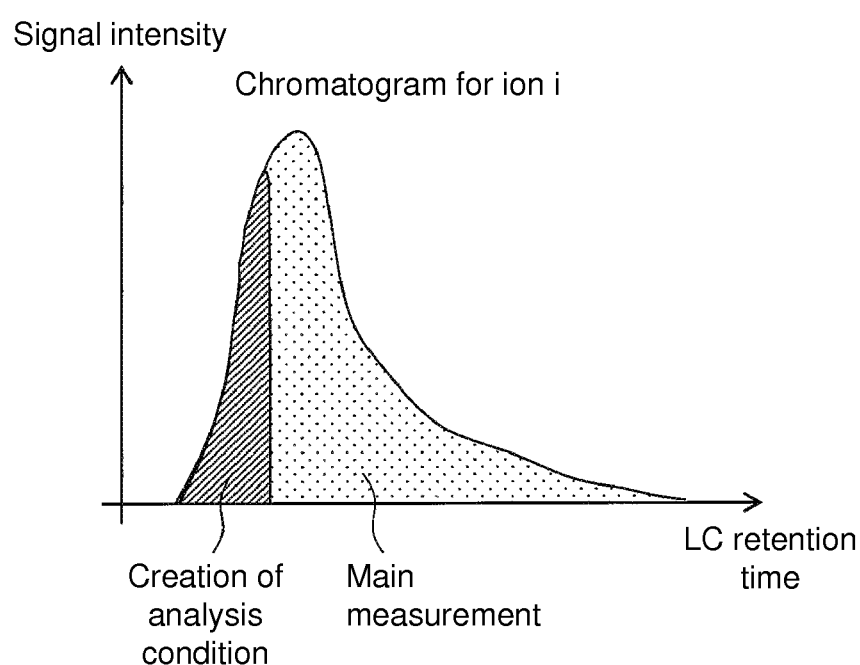
FIG. 18B illustrates a diagram for describing a chromatogram according to a third embodiment.

In the second or a subsequent LC/MS analysis according to the first and the second embodiments, as illustrated in FIG. 18A, the chromatogram of the ion i as the object of measurement is entirely used for the main measurement. According to the present embodiment, as illustrated in FIG. 18B, a method for performing both the analysis condition creation and the main measurement while the ion i is being detected will be described.

In the present method, the creation of the analysis condition and its registration in the database 19 and the main measurement can be performed in a single LC/MS analysis. Accordingly, the method is suitable when only one LC/MS analysis can be performed because of time restrictions, or when the amount of sample is so small that only one LC/MS analysis can be performed, for example. The method may also be suitable for a qualitative analysis, such as a search for the molecular ion species of an unknown sample.

Figure 20:
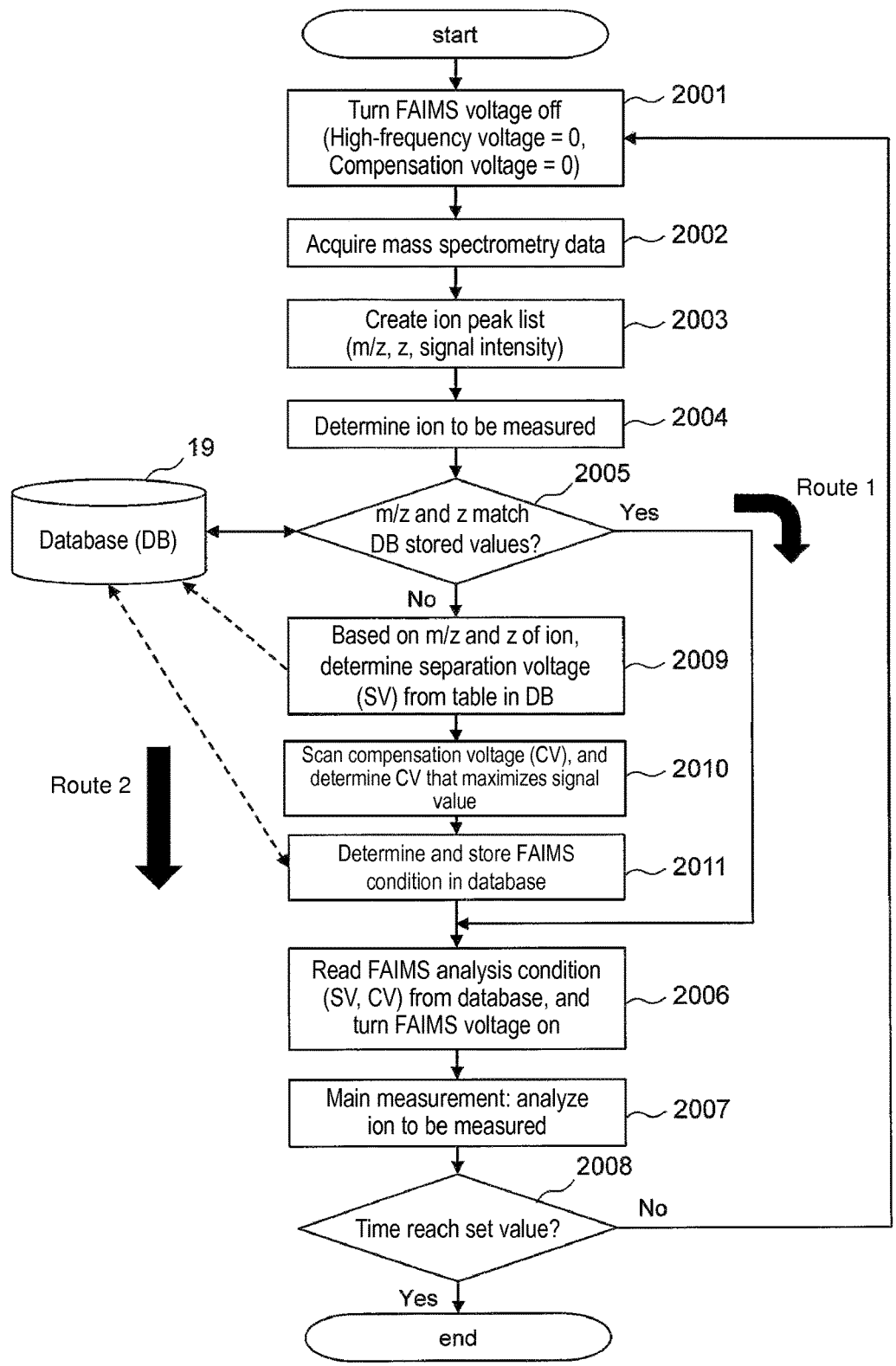
FIG. 20 illustrates an example of the measurement flow of the mass spectrometry system according to a third embodiment.

FIG. 20 illustrates an analysis flow of the present embodiment. Description of steps 2001 to 2004 will be omitted as their contents are similar to those of steps 401 to 404 of FIG. 4. The present embodiment is characterized in that the process branches off to route 1 and route 2 after step 2005.

In step 2005, if the information of the ion to be measured matches stored values in the database 19, the process proceeds to step 2006 (route 1). The flow of steps 2006 to 2008 includes reading the FAIMS analysis condition information from the database 19, setting the analysis condition, and performing the main measurement. Description of steps 2006 to 2008 will be omitted as their contents are similar to those of steps step 406 to 408 of FIG. 4.

In step 2005, if the information of the ion to be measured does not match the FAIMS analysis condition information in the database 19, the process proceeds to step 2009 (route 2).

The flow of steps 2009 to 2011 includes newly creating a FAIMS analysis condition and storing it in the database 19. Description of steps 2009 to 2011 will be omitted as their contents are similar to those of steps 1606 to 1608 of FIG. 16A. The separation voltage and the compensation voltage as the FAIMS analysis condition created in route 2 are stored in the database 19 in step 2011. By storing the analysis condition in the database 19, when the main measurement is performed for the same ion to be measured next time, the analysis condition can be read from the database 19 immediately and then the main measurement can be performed.

In the configuration of the present embodiment, the greater the amount of the ion information (analysis condition) stored in the database 19, the higher the frequency of going through the flow of route 1, and the lower the frequency of going through the flow of route 2. In route 2, steps 2009 to 2011 take time on the order of one second. However, in route 1, the process immediately proceeds to step 2006 to enter the main measurement. Accordingly, the greater the amount of information in the database 19, the more the analysis time can be reduced and the more mass spectra can be acquired, enabling high throughput analysis.

The analysis flow according to the present embodiment will be described with reference to the chromatogram of FIG. 18A and FIG. 18B, which is an example where the chromatogram includes one type of ion i. In route 1, as illustrated in FIG. 18A, the main measurement is started immediately, whereby almost all of the time of ion detection can be used for the main measurement. On the other hand, in route 2, as illustrated in FIG. 18B, the initial several 100 microseconds to several seconds are used for the FAIMS analysis condition search and creation, and thereafter the main measurement is performed. The main measurement is performed until the ion i is not detected anymore, as illustrated. Alternatively, as described above, the main measurement may be performed until the signal intensity drops to a certain value or lower.

As in the foregoing embodiments, besides m/z and the charge amount z, information of the LC retention time may be used as information of the database 19. The details are similar to those of the method described with reference to the first embodiment.

In the present example, when the analysis condition creation and the main analysis are performed as illustrated in the chromatogram of FIG. 20, if the time for analysis condition creation is extended, the time for the main measurement becomes shorter. Thus, by decreasing the time for analysis condition creation as much as possible, the time for the main measurement can be extended, whereby data with higher accuracy can be acquired. The FAIMS analysis condition creation method described in the second embodiment is aimed at achieving such decrease in the time for analysis condition creation. In this way, more time can be allocated for the main measurement, whereby more accurate measurement can be performed.

Thus, there is the problem that, because the main measurement cannot be performed during the time for analysis condition creation, not all of the ion amount can be measured. Namely, as illustrated in FIG. 18B, the main measurement is performed only in the latter half of the chromatogram, with no data being acquired in the first half. Accordingly, a method may be employed whereby the chromatogram for the time for analysis condition creation in the first-half portion is predicted and supplemented from the main measurement data of the latter-half portion.

The shape of the ion chromatogram may be approximated by a function, such as a Gaussian function, an exponential function, a power function, a polynomial, or a combination thereof. Using such function, the amount of ion in the analysis condition creation time is predicted from the result of the main measurement of FIG. 18B to obtain data. In this way, the ion chromatogram can be completely drawn, and the total ion amount can be estimated. Accordingly, the ion amount can be accurately measured, and an increase in determination precision can be expected.

Another example of the second and the third embodiments will be described. In the second and the third embodiments, the separation voltage is unambiguously determined by using the separation voltage table. In the present example, a method will be presented whereby, instead of the unambiguous determination, the optimum separation voltage is determined from a predetermined range including a certain separation voltage. In this way, data acquisition can be performed with high sensitivity and high S/N.

Figure 21:
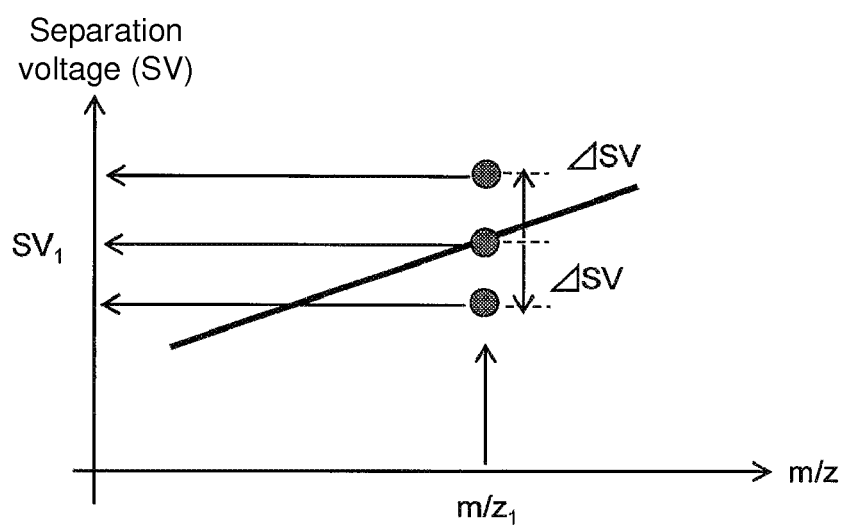
FIG. 21 illustrates another example of the separation voltage determination method.

FIG. 21 is a diagram for describing another example of the separation voltage table. In step 1606 of FIG. 16 or step 2009 of FIG. 20, when the separation voltage is determined from the (m/z, z) of the ion to be measured using the separation voltage table, in addition to the separation voltage obtained from the separation voltage table, separation voltages shifted by predetermined $\pm\Delta S$ V are used for measurement. Specifically, in step 1606 of FIG. 16 or step 2009 of FIG. 20, the separation voltages are determined at the three points of $SV_1$, $SV_1+\Delta SV$, and $SV_1-\Delta SV$.

In step 1607 of FIG. 16 or step 2010 of FIG. 20, the compensation voltage is scanned with respect to each of the three separation voltages, and the relationship between the compensation voltage and the ion signal intensity is plotted. By this process, three items of data as illustrated in FIG. 17B are created. With respect to each of the three data items, the signal intensity when the signal intensity is at a maximum is extracted, and the condition corresponding to the greatest of the three signal intensitys is determined to be the analysis condition for the object of measurement. Specifically, the separation voltages of a predetermined range are initially determined from the separation voltage table, and compensation voltages in the predetermined range are scanned to eventually determine the optimum separation voltage and compensation voltage. The determined separation voltage and compensation voltage are stored in the database 19. In this method, the separation voltage can be optimized with increased accuracy. In another method, the optimum condition may be determined by considering not only the signal intensity of the three data items as illustrated in FIG. 17B, which are compensation voltage-dependent, but also resolution as described above.

The present invention is not limited to any of the above-described embodiments and may include various modifications. The embodiments have been described for facilitating an understanding of the present invention, and are not necessarily limited to include all of the described configurations. A part of the configuration of one embodiment may be replaced by the configuration of another embodiment, or the configuration of the other embodiment may be incorporated into the configuration of the one embodiment. With respect to a part of the configuration of each embodiment, addition of another configuration, deletion, or substitution may be possible.

For example, in terms of being able to determine the analysis condition suitable for the ion to be measured in a short time, an analysis system may be provided with at least: a storage unit having a database 19 stored therein associating mass spectrometry result information with an analysis condition concerning ion mobility separation; and a control unit that determines, as the analysis condition for an ion to be measured, the analysis condition associated with the mass spectrometry result information in the database 19 corresponding to the mass spectrometry result information of the ion to be measured.

The control lines or information lines in the drawings are those considered to be necessary for description purposes, and do not necessarily represent all of the control lines or information lines found in a product. All of the configurations may be mutually connected.

REFERENCE SIGNS LIST

1 First electrode
2 Second electrode
3 Alternating-current voltage power supply
4 Direct-current voltage power supply
5 Ion
6 Ion trajectory
10 Mass spectrometry system
11 Pre-processing unit
12 Ionization unit
13 Ion mobility separation unit
14 Mass spectrometry unit
15 Ion detection unit
16 Data processing unit
17 Display unit
18 Control unit
19 Database
20 Input unit
21 Sample

The invention claimed is:

1. An analysis system comprising:
a storage unit that stores first information associating mass spectrometry result information with an analysis condition concerning ion mobility separation and second information associating a mass-to-charge ratio with a separation voltage;
a control unit that determines, as a first analysis condition for an ion to be measured, the analysis condition associated with the mass spectrometry result information of the first information corresponding to the mass spectrometry result information of the ion to be measured;
an ion mobility separation unit that subjects an ion to ion mobility separation;
a mass spectrometry unit that subjects the ion that has been subjected to the ion mobility separation to mass separation; and
an ion detection unit that detects the mass-separated ion, wherein
the mass spectrometry result information of the ion to be measured includes the mass-to-charge ratio and a charge;
the control unit determines, as the first analysis condition, a first separation voltage associated with the mass-to-charge ratio of the second information corresponding to the mass-to-charge ratio of the ion to be measured;
the control unit determines, in the absence of the mass spectrometry result information of the first information corresponding to the mass spectrometry result information of the ion to be measured, the first separation voltage in the second information as the first analysis condition; and
the control unit stores the first analysis condition in the storage unit as the first information.

2. The analysis system according to claim 1, wherein:
the mass spectrometry result information of the first information and the mass spectrometry result information of the ion to be measured include information of a mass-to-charge ratio and a charge amount, or information of a mass-to-charge ratio, a charge amount, and a time of elution of a sample from a liquid chromatograph column (LC retention time).

3. The analysis system according to claim 2, wherein the control unit corrects the mass-to-charge ratio or the LC retention time.

4. The analysis system according to claim 3, wherein the control unit corrects the mass-to-charge ratio or the LC retention time using a peak of at least one correction sample in a mass spectrum.

5. The analysis system according to claim 3, wherein, when the control unit corrects the LC retention time, the LC retention time is corrected using a relationship between the LC retention time and a solvent mixture ratio.

6. The analysis system according to claim 1, wherein the control unit determines at least one ion to be measured from a plurality of ions using an ion signal intensity in a mass spectrum or a signal to noise ratio.

7. The analysis system according to claim 1,
wherein the control unit executes an analysis process with respect to the ion to be measured using the first analysis condition.

8. The analysis system according to claim 7, wherein the control unit terminates the analysis process with respect to the ion to be measured when a predetermined termination condition is satisfied.

9. The analysis system according to claim 8, wherein the predetermined termination condition is a condition concerning a signal intensity in a mass spectrum of the ion to be measured.

10. An analysis system comprising:
a storage unit that stores first information associating mass spectrometry result information with an analysis condition concerning ion mobility separation;
a control unit that determines, as a first analysis condition for an ion to be measured, the analysis condition associated with the mass spectrometry result information of the first information corresponding to the mass spectrometry result information of the ion to be measured;
an ion mobility separation unit that subjects an ion to ion mobility separation;
a mass spectrometry unit that subjects the ion that has been subjected to the ion mobility separation to mass separation; and
an ion detection unit that detects the mass-separated ion,
wherein the control unit executes an analysis process with respect to the ion to be measured using the first analysis condition; and
wherein the control unit determines the first analysis condition in a first liquid chromatograph measurement (LC measurement), and executes the analysis process with respect to the ion to be measured in a second or a subsequent LC measurement; and
wherein the control unit scans a plurality of compensation voltages with respect to the ion to be measured while applying the first separation voltage, determines a first compensation voltage on the basis of an ion signal intensity at the plurality of compensation voltages, and determines the first compensation voltage as the first analysis condition.

11. An analysis system comprising:
a storage unit that stores first information associating mass spectrometry result information with an analysis condition concerning ion mobility separation;
a control unit that determines, as a first analysis condition for an ion to be measured, the analysis condition associated with the mass spectrometry result information of the first information corresponding to the mass spectrometry result information of the ion to be measured;
an ion mobility separation unit that subjects an ion to ion mobility separation;
a mass spectrometry unit that subjects the ion that has been subjected to the ion mobility separation to mass separation; and
an ion detection unit that detects the mass-separated ion,
wherein the control unit executes an analysis process with respect to the ion to be measured using the first analysis condition;
wherein the control unit determines the first analysis condition and executes the analysis process with respect to the ion to be measured during a first liquid chromatograph measurement (LC measurement); and
wherein the control unit scans a plurality of compensation voltages with respect to the ion to be measured while applying a predetermined separation voltage range including the first separation voltage, determines a first compensation voltage on the basis of the signal intensity of the ion to be measured at the plurality of compensation voltages, and determines the first compensation voltage as the first analysis condition.

12. An analysis system comprising:
a storage unit that stores first information associating mass spectrometry result information with an analysis condition concerning ion mobility separation and second information associating a mass-to-charge ratio with a separation voltage;
a control unit that determines, as a first analysis condition for an ion to be measured, the analysis condition associated with the mass spectrometry result information of the first information corresponding to the mass spectrometry result information of the ion to be measured;
an ion mobility separation unit that subjects an ion to ion mobility separation;
a mass spectrometry unit that subjects the ion that has been subjected to the ion mobility separation to mass separation; and
an ion detection unit that detects the mass-separated ion, wherein
the mass spectrometry result information of the ion to be measured includes the mass-to-charge ratio and a charge;
the control unit determines, as the first analysis condition, a first separation voltage associated with the mass-to-charge ratio of the second information corresponding to the mass-to-charge ratio of the ion to be measured; and
the control unit scans a plurality of compensation voltages with respect to the ion to be measured while applying the first separation voltage, determines a first compensation voltage on the basis of an ion signal intensity at the plurality of compensation voltages, and determines the first compensation voltage as the first analysis condition.

13. An analysis system comprising:
a storage unit that stores first information associating mass spectrometry result information with an analysis condition concerning ion mobility separation and second information associating a mass-to-charge ratio with a separation voltage;
a control unit that determines, as a first analysis condition for an ion to be measured, the analysis condition associated with the mass spectrometry result information of the first information corresponding to the mass spectrometry result information of the ion to be measured;
an ion mobility separation unit that subjects an ion to ion mobility separation;
a mass spectrometry unit that subjects the ion that has been subjected to the ion mobility separation to mass separation; and
an ion detection unit that detects the mass-separated ion, wherein
the mass spectrometry result information of the ion to be measured includes the mass-to-charge ratio and a charge;
the control unit determines, as the first analysis condition, a first separation voltage associated with the mass-to-charge ratio of the second information corresponding to the mass-to-charge ratio of the ion to be measured; and
wherein the control unit scans a plurality of compensation voltages with respect to the ion to be measured while applying a predetermined separation voltage range including the first separation voltage, determines a first compensation voltage on the basis of the signal intensity of the ion to be measured at the plurality of compensation voltages, and determines the first compensation voltage as the first analysis condition.

* * * * *